US007989495B2

(12) United States Patent
Kuwada

(10) Patent No.: US 7,989,495 B2
(45) Date of Patent: Aug. 2, 2011

(54) COMPOSITIONS AND METHODS FOR INHIBITING NF-κB MEDIATED TUMORIGENICITY AND ADHESION DEPENDENT SURVIVAL OF CANCER CELLS

(75) Inventor: Scott K. Kuwada, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 737 days.

(21) Appl. No.: 10/505,244

(22) PCT Filed: Feb. 21, 2003

(86) PCT No.: PCT/US03/05372
§ 371 (c)(1),
(2), (4) Date: Jan. 18, 2005

(87) PCT Pub. No.: WO03/072038
PCT Pub. Date: Sep. 4, 2003

(65) Prior Publication Data
US 2005/0124590 A1 Jun. 9, 2005

Related U.S. Application Data

(60) Provisional application No. 60/358,853, filed on Feb. 21, 2002.

(51) Int. Cl.
*A61K 31/66* (2006.01)
*A61K 31/275* (2006.01)
*A61K 31/18* (2006.01)
*A61K 31/10* (2006.01)

(52) U.S. Cl. ......... 514/520; 514/519; 514/602; 514/708

(58) Field of Classification Search .................. None
See application file for complete search history.

(56) References Cited

U.S. PATENT DOCUMENTS
7,175,679 B2 * 2/2007 Khan et al. .............. 514/2

OTHER PUBLICATIONS

Biswas, Debajit K., Sun-Chun Dai, Antonio Cruz, Barbara Weiser, Edgard Graner and Arther B. Pardee. The nuclear factor kapp B (NF-kB): A potential therapeutical target for estrogen receptor. vol. 98. No. 18. 2001. 10386-10391. 6 sheets*
Izban et al. Constitutive Expression of NF-kappaB is a characteristic feature of mycosis fungoides: implications for apoptosis resistance and pathogenesis. Human Pathology. vol. 31, No. 12 (Dec. 2000).*
Goodman et al. [Editors] "Chapter 198: Principles of Cancer Therapy." Cecil's Textbook Medicine (Twenty-First Edition, vol. 1). W.B. Saunders Company, 2000. pp. 1060-1074.*
Lawrence et al. Possible new role for NK-kappaB in the resolution of inflammation. Nature Medicine. vol. 7, No. 12, Dec. 2001.*
Alkalay et al. (1995). Stimulation-dependent I kappa B alpha phosphorylation marks the NF-B inhibitor for degradation via the ubiquitin-proteasome pathway, Proc Natl Acad Sci U S A 92; 10599-10603.
Aoudjit and Vuori, (2001). Matrix attachment regulates Fas-induced apoptosis in endothelial cells: a role for c-flip and implications for anoikis, J Cell Biol 152, 633-643.
Battu et al. (1998). Cyclooxygenase-2 expression in human adenocarcinoma cell line HT29 cl.19A, Anticancer Res 18, 2397-2403.
Beg et al. (1992). I kappa B interacts with the nuclear localization sequences of the subunits of NF-κB: a mechanism for cytoplasmic retention, Genes Dev 6, 1899-1913.
Boland, (1999). Malignant Tumors of the Colon. In Textbook of Gastroenterology, T. Yamada, D. H. Alpers, L. Laine, C. Owyang, and D. W. Powell, eds. (Philadelphia, Lippincott Williams and Wilkins), pp. 2023-2082.
Cao et al. (1998). Interleukin 15 protects against toxicity and potentiates antitumor activity of 5-fluorouracil alone and in combination with leucovorin in rats bearing colorectal cancer, Cancer Res 58, 1695-1699.
Chambers et al. (1995). Steps in tumor metastasis: new concepts from intravital videomicroscopy, Cancer Metastasis Rev 14, 279-301.
Chen et al. (1995). Signal-induced site-specific phosphorylation targets I kappa B alpha to the ubiquitin-proteasome pathway, Genes Dev 9, 1586-1597.
Crofford et al. (1997). Involvement of nuclear factor κ B in the regulation of cyclooxygenase-2 expression by interleukin-1 in rheumatoid synoviocytes, Arthritis Rheum 40, 226-236.
Darmoul et al. (2001). Initiation of human colon cancer cell proliferation by trypsin acting at protease-activated receptor-2, Br J Cancer 85, 772-779.
D'Haens et al. (1999). Endoscopic and histological healing with infliximab anti-tumor necrosis factor antibodies in Crohn's disease: A European multicenter trial, Gastroenterology 116, 1029-1034.
DiDonato et al. 1996). Mapping of the inducible IkappaB phosphorylation sites that signal its ubiquitination and degradation, Mol Cell Biol 16, 1295-1304.
DuBois et al. (1996). Nonsteroidal anti-inflammatory drugs, eicosanoids, and colorectal cancer prevention, Gastroenterol Clin North Am 25, 773-791.
Eberhart et al. (1994). Up-regulation of cyclooxygenase 2 gene expression in human colorectal adenomas and adenocarcinomas, Gastroenterology 107, 1183-1188.
Elder et al. (1997). Induction of apoptotic cell death in human colorectal carcinoma cell lines by a cyclooxygenase-2 (COX-2)-selective nonsteroidal anti- inflammatory drug: independence from COX-2 protein expression, Clin Cancer Res 3, 1679-1683.
Elnemr et al. (2001). Human pancreatic cancer cells disable function of Fas receptors at several levels in Fas signal transduction pathway, Int J Oncol 18, 311-316.
Engers and Gabbert, (2000). Mechanisms of tumor metastasis: cell biological aspects and clinical implications, J Cancer Res Clin Oncol 126, 682-692.
Frisch and Francis, (1994). Disruption of epithelial cell-matrix interactions induces apoptosis, J Cell Biol 124, 619-626.
Girl and Aggarwal, (1998). Constitutive activation of NF-κB causes resistance to apoptosis in human cutaneous T cell lymphoma HuT-78 cells. Autocrine role of tumor necrosis factor and reactive oxygen intermediates, J Biol Chem 273, 14008-14014.

(Continued)

Primary Examiner — Brandon J Fetterolf
Assistant Examiner — Anna Pagonakis
(74) Attorney, Agent, or Firm — Ballard Spahr LLP

(57) ABSTRACT

Disclosed are compositions and methods for inhibiting NF-κB mediated cellular proliferation and metastasis.

8 Claims, 14 Drawing Sheets

OTHER PUBLICATIONS

Figure 1A:
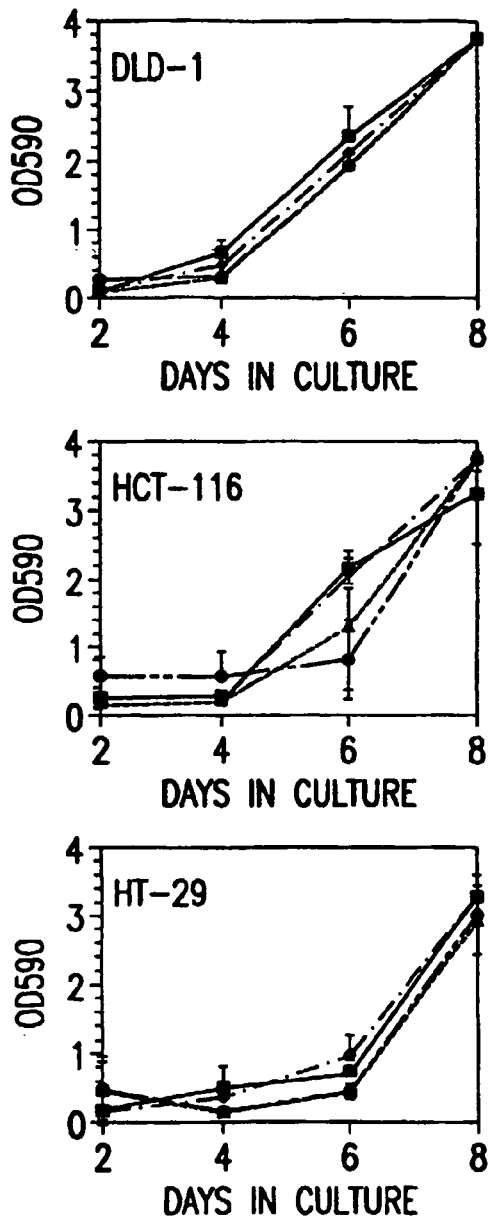

Golab et al. (2000). Interleukin 12 and indomethacin exert a synergistic, angiogenesis-dependent antitumor activity in mice, Life Sci 66, 1223-1230.

Groden et al. (1995). Response of colon cancer cell lines to the introduction of APC, a colon-specific tumor suppressor gene, Cancer Res 55, 1531-1539.

Han et al. (2000). Activation of NF-κB determines the sensitivity of human colon cancer cells to TNFalpha-induced apoptosis, Biol Pharm Bull 23, 420-426.

Hansen et al. (1995). Tumor cells in blood shed from the surgical field, Arch Surg 130, 387-393.

Hansen et al. (1999). Blood irradiation for intraoperative autotransfusion in cancer surgery: demonstration of efficient elimination of contaminating tumor cells, Transfusion 39, 608-615.

He et al. (1999). PPARdelta is an APC-regulated target of nonsteroidal anti-inflammatory drugs, Cell 99, 335-345.

Henkel et al. (1993). Rapid proteolysis of I kappa B-alpha is necessary for activation of transcription factor NF-κB, Nature 365, 182-185.

Higgins et al. (1993). Antisense inhibition of the p65 subunit of NF-κB blocks tumorigenicity and causes tumor regression, Proc Natl Acad Sci U S A 90, 9901-9905.

Hsi et al. 2000). Lack of cyclooxygenase-2 activity in HT-29 human colorectal carcinoma cells, Exp Cell Res 256, 563-570.

Huang et al. (2001). Blockade of NF-κB activity in human prostate cancer cells is associated with suppression of angiogenesis, invasion, and metastasis, Oncogene 20, 4188-4197.

Ichijo et al.. (1997). Induction of apoptosis by ASK1, a mammalian MAPKKK that activates SAPK/JNK and p38 signaling pathways, Science 275, 90-94.

Ilyas et al.. (1997). Beta-catenin mutations in cell lines established from human colorectal cancers, Proc Natl Acad Sci U S A 94, 10330-10334.

Irmler et al. (1997). Inhibition of death receptor signals by cellular FLIP, Nature 388, 190-195.

Jung et al. (1995). A distinct array of proinflammatory cytokines is expressed in human colon epithelial cells in response to bacterial invasion, J Clin Invest 95, 55-65.

Kreuz et al. (2001). NF-κB inducers upregulate cFLIP, a cycloheximide-sensitive inhibitor of death receptor signaling, Mol Cell Biol 21, 3964-3973.

Kutchera et al. (1996). Prostaglandin H synthase 2 is expressed abnormally in human colon cancer: evidence for a transcriptional effect, Proc Natl Acad Sci U S A 93, 4816-4820.

Lee and Juliano, (2000). alpha5beta1 integrin protects intestinal epithelial cells from apoptosis through a phosphatidylinositol 3-kinase and protein kinase B- dependent pathway, Mol Biol Cell 11, 1973-1987.

Liefers et al. (1998). Micrometastases and survival in stage II colorectal cancer, N Engl J Med 339, 223-228.

Liotta et al. (1974). Quantitative relationships of intravascular tumor cells, tumor vessels, and pulmonary metastases following tumor implantation, Cancer Res 34, 997-1004.

Martin, (1996). Normal Cells and Cancer Cells. In Molecular Oncology, J. M. Bishop, and R. A. Weinberg, eds. (New York, Scientific American), pp. 13-40.

Mehes et al. (2001). Circulating breast cancer cells are frequently apoptotic, Am J Pathol 159, 17-20.

Meredith et al. (1993). The extracellular matrix as a cell survival factor, Mol Biol Cell 4, 953-961.

Munemitsu et al. (1995). Regulation of intracellular beta-catenin levels by the adenomatous polyposis coli (APC) tumor-suppressor protein, Proc Natl Acad Sci U S A 92, 3046-3050.

Newton et al. (1997). Evidence for involvement of NF-B in the transcriptional control of COX-2 gene expression by IL-1beta, Biochem Biophys Res Commun 237, 28-32.

Newton et al. (1997). Superinduction of COX-2 mRNA by cycloheximide and interleukin-1beta involves increased transcription and correlates with increased NF-κB and JNK activation, FEBS Lett 418, 135-138.

Nicolson, (1991). Gene expression, cellular diversification and tumor progression to the metastatic phenotype, Bioessays 13, 337-342.

Palombella et al. (1994). The ubiquitin-proteasome pathway is required for processing the NF-B 1 precursor protein and the activation of NF-κB, Cell 78, 773-785.

Peleg et al. (1996). Long-term use of nonsteroidal antiinflammatory drugs and other chemopreventors and risk of subsequent colorectal neoplasia, Dig Dis Sci 41, 1319-1326.

Pierce et al. (1997). Novel inhibitors of cytokine-induced IkappaBalpha phosphorylation and endothelial cell adhesion molecule expression show anti-inflammatory effects in vivo, J Biol Chem 272, 21096-21103.

Remacle-Bonnet et al. (2000). Insulin-like growth factor-I protects colon cancer cells from death factor-induced apoptosis by potentiating tumor necrosis factor alpha- induced mitogen-activated protein kinase and nuclea factor kappaB signaling pathways, Cancer Res 60, 2007-2017.

Renard et al. (2001). Development of a sensitive multi-well colorimetric assay for active NF-κB, Nucleic Acids Res 29, No. 4e21.

Rosette and Karin, (1996). Ultraviolet light and osmotic stress: activation of the JNK cascade through multiple growth factor and cytokine receptors, Science 274, 1194-1197.

Rubinfeld et al. (1995). The APC protein and E-cadherin form similar but independent complexes with alpha-catenin, beta-catenin, and plakoglobin, J Biol Chem 270, 5549-5555.

Ryu et al. (2001). Increased expression of cFLIP(L) in colonic adenocarcinoma, J Pathol 194, 15-19.

Schmedtje et al. (1997). Hypoxia induces cyclooxygenase-2 via the NF-κB p65 transcription factor in human vascular endothelial cells, J Biol Chem 272, 601-608.

Schwartz et al. (1999). The role of NF-κB / IκB proteins in cancer: implications for novel treatment strategies., Surgical Oncology 8, 143-153.

Shanmugathasan and Jothy, (2000). Apoptosis, anoikis and their relevance to the pathobiology of colon cancer, Pathol Int 50, 273-279.

Shao et al. (2000). Regulation of constitutive cyclooxygenase-2 expression in colon carcinoma cells, J Biol Chem 275, 33951-33956.

Sheng et al. (1997). Inhibition of human colon cancer cell growth by selective inhibition of cyclooxygenase-2, J Clin Invest 99, 2254-2259.

Shiff et al. (1995). Sulindac sulfide, an aspirin-like compound, inhibits proliferation, causes cell cycle quiescence, and induces apoptosis in HT-29 colon adenocarcinoma cells, J Clin Invest 96, 491-503.

Shinohara et al. (1998). Prevention of intestinal toxic effects and intensification of irinotecan's therapeutic efficacy against murine colon cancer liver metastases by oral administration of the lipopeptide JBT 3002, Clin Cancer Res 4, 2053-2063.

Shureiqi et al. (1999). Decreased 13-S-hydroxyoctadecadienoic acid levels and 15-lipoxygenase-1 expression in human colon cancers, Carcinogenesis 20, 1985-1995.

Shureiqi et al. (2000). 15-LOX-1: a novel molecular target of nonsteroidal anti-inflammatory drug-induced apoptosis in colorectal cancer cells, J Natl Cancer Inst 92, 1136-1142.

Singh and Trotman, (1998). Use and safety of aspirin in the chemoprevention of colorectal cancer, J Assoc Acad Minor Phys 9, 40-44.

Sinicrope et al. (1996). Phase I trial of sulindac plus 5-fluorouracil and levamisole: potential adjuvant therapy for colon carcinoma, Clin Cancer Res 2, 37-41.

Smalley and DuBois, (1997). Colorectal cancer and nonsteroidal anti-inflammatory drugs, Adv Pharmacol 39, 1-20.

Sokoloski et al. (1993). Antisense oligonucleotides to the p65 subunit of NF-κB block CD11b expression and alter adhesion properties of differentiated HL-60 granulocytes, Blood 82, 625-632.

Stehlik et al. (1998). Nuclear factor (NF)-kappaB-regulated X-chromosome-linked iap gene expression protects endothelial cells from tumor necrosis factor alpha- induced apoptosis, J Exp Med 188, 211-216.

Strater et al. (1996). Rapid onset of apoptosis in vitro follows disruption of beta 1- integrin/matrix interactions in human colonic crypt cells, Gastroenterology 110, 1776-1784.

Tepper and Seldin, (1999). Modulation of caspase-8 and FLICE-inhibitory protein expression as a potential mechanism of Epstein-Barr virus tumorigenesis in Burkitt's lymphoma, Blood 94, 1727-1737.

Traenckner et al. 1995). Phosphorylation of human IκB-alpha on serines 32 and 36 controls I kappa B-alpha proteolysis and NF-κB activation in response to diverse stimuli, Embo J 14, 2876-2883.

Tsuji et al. (1996). Evidences for involvement of cyclooxygenase-2 in proliferation of two gastrointestinal cancer cell lines, Prostaglandins Leukot Essent Fatty Acids 55, 179-183.

Tsujii and DuBois, (1995). Alterations in cellular adhesion and apoptosis in epithelial cells overexpressing prostaglandin endoperoxide synthase 2, Cell 83, 493-501.

Wang et al. (1999). Control of inducible chemoresistance: enhanced anti-tumor therapy through increased apoptosis by inhibition of NF-κB, Nat Med 5, 412-417.

Wang, et al. (1998). NF-κB antiapoptosis: induction of TRAF1 and TRAF2 and c-IAP1 and c-IAP2 to suppress caspase-8 activation, Science 281, 1680-1683.

Weiss, (1985). Metastatic inefficiency. In Liver Metastasis, L. Weiss, and H. Gilbert, eds. (Boston, Hall), pp. 126-157.

Wu et al. (1998). IEX-1L, an apoptosis inhibitor involved in NF-κB -mediated cell survival, Science 281, 998-1001.

Yamamoto et al. (1999). Sulindac inhibits activation of the NF-κB pathway, J Biol Chem 274, 27307-27314.

Yin et al. (1998). The anti-inflammatory agents aspirin and salicylate inhibit the activity of IκB kinase-beta, Nature 396, 77-80.

Hu et al., "An IκBα Inhibitor Causes Leukemia Cell Death through a p38 MAP Kinase-dependent, NF-κB-Independent Mechanism," *Cancer Res* 61:6290-6296, 2001.

Cory et al., "Implications of the Involvement of the Endoplasmic Reticulum Stress Pathway in Drug-Induced Apoptosis," *Anticancer Res* 28(2A):681-686, 2008.

Vega et al., "Rituximab-Induced Inhibityion of YY1 and Bcl-$x_L$ Expression in Ramos Non-Hodgkin's Lymphoma Cell Line via Inhibition of NF-κB Activity: Role of YY1 and Bcl-$x_L$ in Fas Resistance and Chemoresistance, Respectively," *J Immunol* 175:2174-2183, 2005.

Huerta-Yepez et al., "Nitric oxide sensitizes prostate carcinoma cell lines to TRAIL-mediates apoptosis via inactivation of NF-κB and inhibition of Bcl-$x_L$ expression," *Oncogene* 23:4993-5003, 2004.

Mabuchi et al., "Inhibition of NF-κB Increases the Efficacy of Cisplatin in inVitro and in Vivo Ovarian Cancer Models," *J Biol Chem* 279:23477-23485, 2004.

El-Rages et al., "Phase II study of dose attenuated schedule of irinotecan, capecitabine, and celecoxib in advanced colorectal cancer," *Cancer Chemother Pharmacol* 61:283-289, 2008.

Becerra et al., "Increased Toxicity and Lack of Efficacy of Rofecoxib in Combination with Chemotherapy for Treatment of Metastatic Colorectal Cancer: A Phase II Study," *Int J Cancer* 105:868-872, 2003.

Canadian Intellectual Property Office, Official Action issued in Canadian Application No. 2,477,172 on Nov. 3, 2009.

Ghanim et al., Supression of nuclear factor-kappaB and stimulation of inhibitor kappaB by troglitazone:evidence for an anti-inflammatory effect and potential antiatherosclerotic effect in the obese, J. Clin. Endocrinol. Metab., 86(3):1306-12, 2001.

Hazzalin et al., "Anisomycin selectively desensitizes signaling components involved in stress kinase activation and fos and jun induction," Mol. Cell. Biol., 18(4):1844-54, 1998.

International Search Authority, International Search Report and Written Opinion for PCT/US2009/039508 mailed Sep. 24, 2009.

Scaife et al., "Nuclear Factor B Inhibitors Induce Adhesion-dependent Colon Cancer Apoptosis: Implications for Metastasis," *Cancer Res.* 62:6870-6878, Dec. 1, 2002.

\* cited by examiner

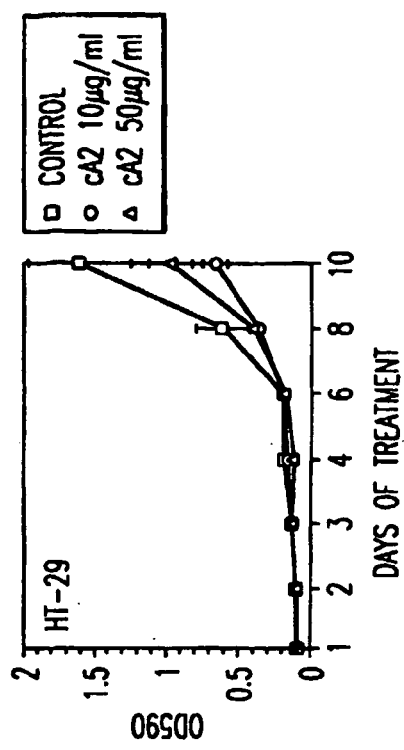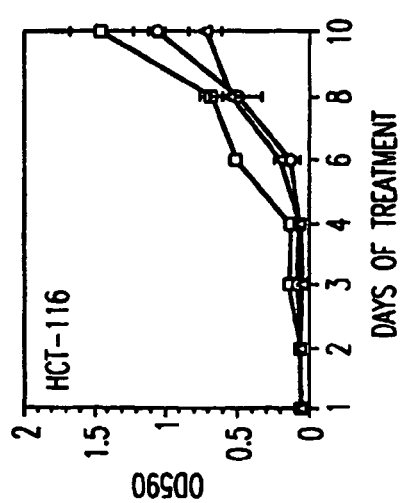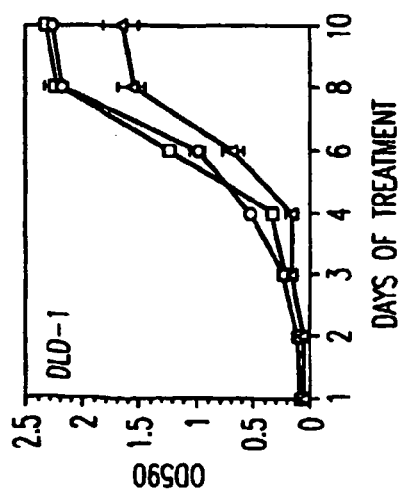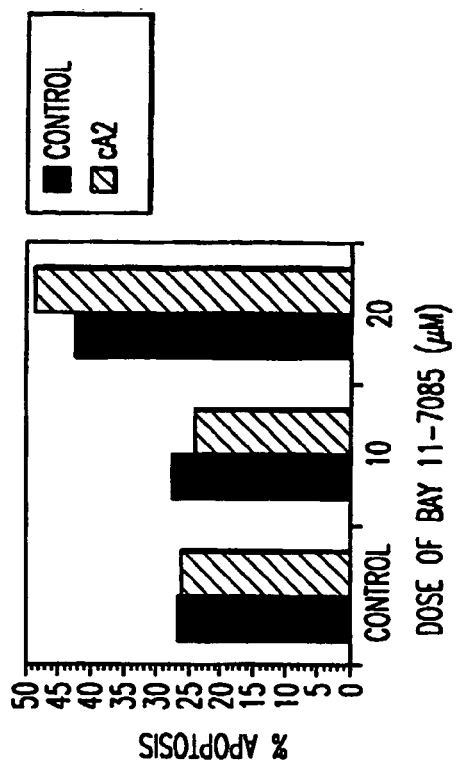

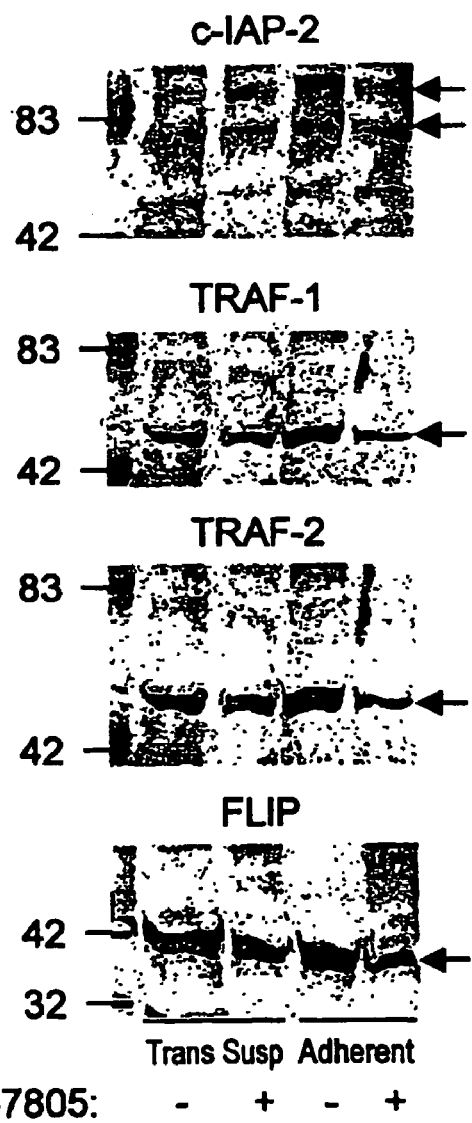
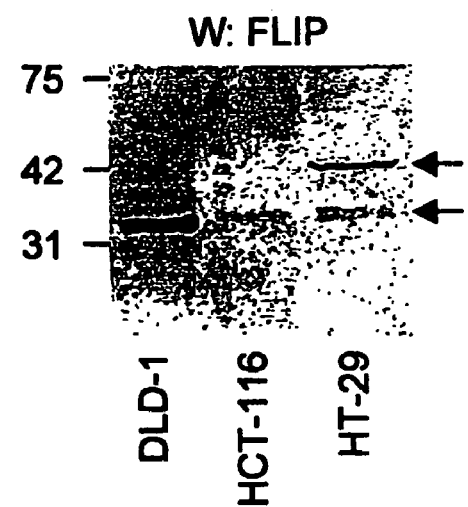
FIG. 7C
FIG. 7D

COMPOSITIONS AND METHODS FOR INHIBITING NF-κB MEDIATED TUMORIGENICITY AND ADHESION DEPENDENT SURVIVAL OF CANCER CELLS

CROSS REFERENCE TO RELATED APPLICATIONS

This application claims priority to U.S. Provisional Application Ser. No. 60/358,853, filed on Feb. 21, 2002, which is herein incorporated by reference in its entirety.

I. BACKGROUND

Many adherent cells undergo apoptosis when converted to suspension culture or when detached from the underlying extracellular matrix. (Strater et al., 1996) This process has been termed anoikis and may be an important mechanism of tissue homeostasis. (Frisch and Francis, 1994) Cancer cells, on the other hand, have long been known for their ability to grow in the absence of adhesion, a characteristic known as anchorage-independent proliferation. (Martin, 1996) This is of clinical relevance to metastasis, because cancer cells must transiently survive in the absence of adhesion as they travel to and migrate into distant tissues via the circulatory or lymphatic systems. Efforts to curb metastasis are critical since the presence of metastases is the single most important prognostic indicator for survival in cancer patients. Preventing metastasis of primary tumors is hampered by the apparent ease by which cancer cells gain access to the circulatory system either naturally or at the time of surgical resection. (Hansen et al., 1999; Hansen et al., 1995; Mehes et al., 2001) Iatrogenic seeding of cancer cells is particularly worrisome as the primary modality of therapy for most resectable solid tumors is surgery.

Disclosed are compositions and methods related to inhibiting the affect of NF-κB on cancer, through inhibition of metastasis, readhesion, and cancer cell proliferation.

II. SUMMARY

The disclosed compositions and methods are related to the treatment and inhibition of cancer.

III. BRIEF DESCRIPTION OF THE DRAWINGS

Figure 1B:
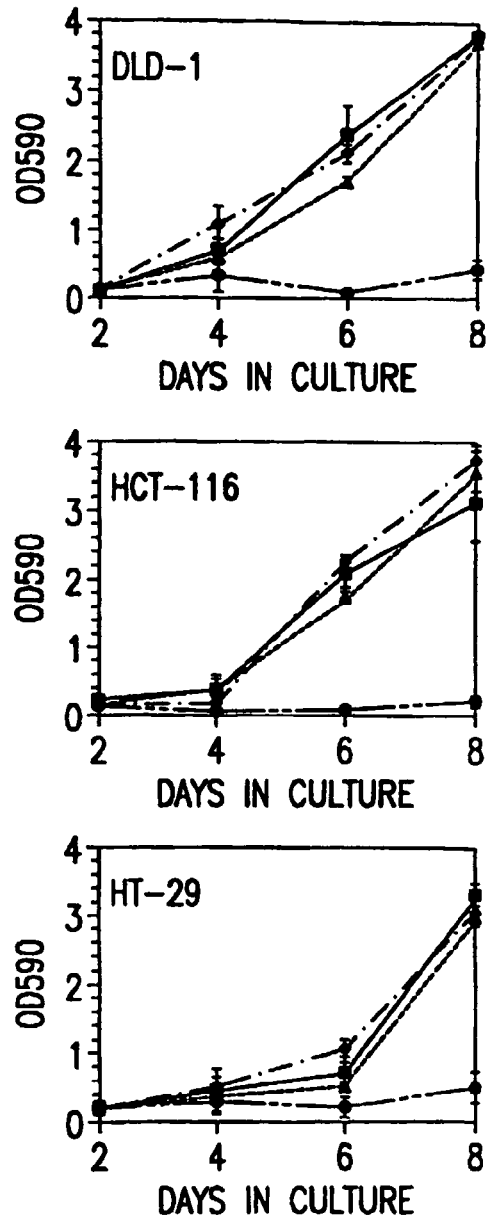
Figure 1C:
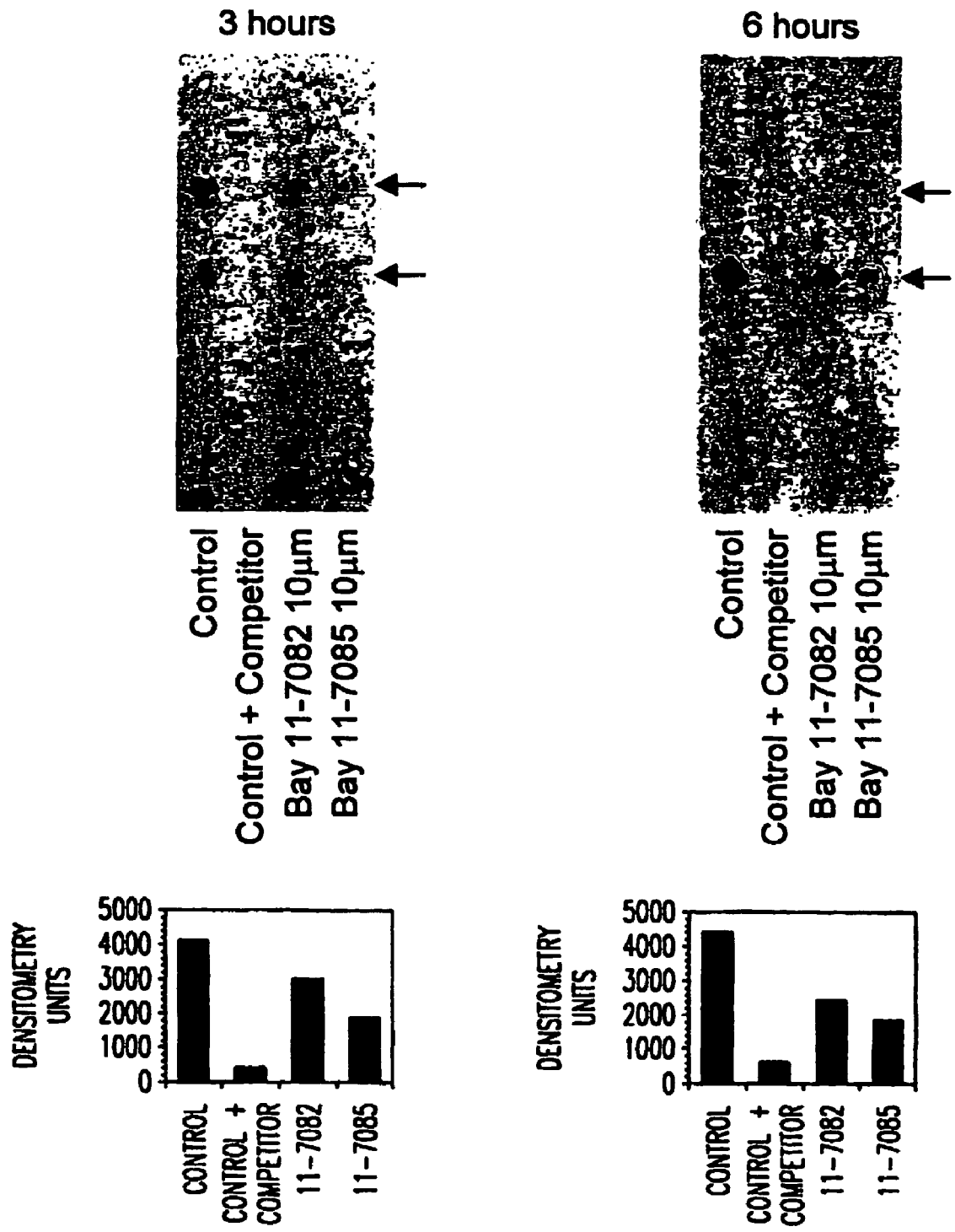

FIG. 1 shows the effect of NF-κB inhibitors on colon cancer cell proliferation. DLD-1, HCT-116, and HT-29 were cultured on 96-well plates in the presence or absence of BAY 11-7082 (A) or BAY 11-7085 (B) for 8 days. The cells were fixed, stained with crystal violet, solubilized in deoxycholate, and read in a spectrophotometer at 590 nm. Legend: control (DMSO) squares, BAY 0.1 μM diamonds, BAY 1.0 μM triangles, BAY 10.0 μM ovals. The data points represent the mean values of experiments performed in triplicate and the error bars the standard error of the means. FIG. 1C shows electrophoretic mobility shift assays showing inhibition of NF-κB binding to an NF-κB DNA consensus oligonucleotide in nuclear lysates from HT-29 cells treated with BAY 11-7082 or BAY 11-7085 for 3 (left panel) or 6 (right panel) hours. The figure shows the typical results of four experiments. The densitometry data of the gels are shown in graphic form at the bottom of the figure. Excess cold competitor DNA oligonucleotide was used to demonstrate the specificity of the protein-DNA binding.

Figure 2A:
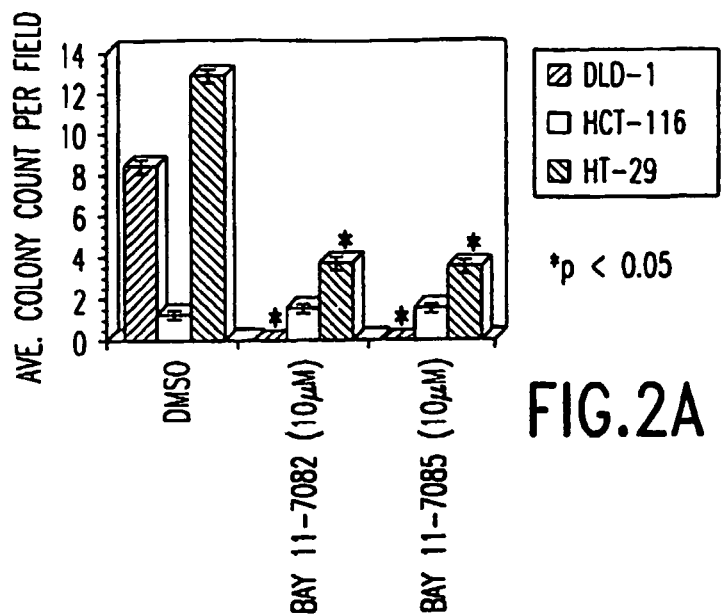
Figure 2B:
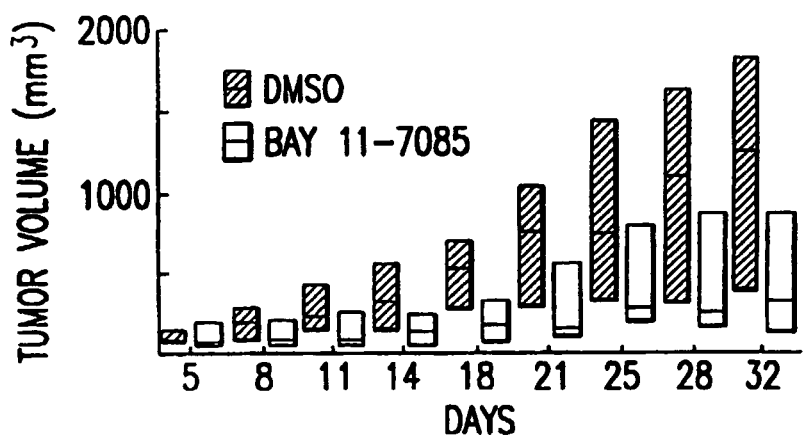

FIG. 2A shows NF-κB inhibitors, BAY 11-7082 and BAY 11-7085, decrease anchorage-independent proliferation of colon cancer cells. DLD-1, HCT-116, and HT-29 cells were cultured for 6 days in soft agar in the presence of DMSO (control), 10 μM BAY 11-7082, or 10 μM BAY 11-7085. The data points represent the means of colony counts per field (20×) performed in 5 different regions of the culture dishes. The data shown represent a typical result of two separate experiments. FIGS. 2B,C, show athymic mice received subcutaneous injections of HT-29 (B) or HCT-116 (C) cells, followed by 5 mg/ml of BAY 11-7085 (dark bars) or DMSO (white bars) intraperitoneally twice weekly. The bars represent the 25-75% ranges of the tumor volumes and the horizontal lines in the bars are the medians. Using the Kruskal-Wallace statistical test to compare the median tumor volumes between BAY 11-7085 and DMSO yielded a p-value of 0.005 for HT-29 cells but >0.05 for HCT-116 cells.

FIG. 3 shows NF-κB inhibitors cause apoptosis of colon cancer cells. FIG. 3A shows adherent and HT-29 cells were treated with DMSO alone (control), 10 and 20 μM BAY 11-7085, or 20 μM MG-132 for 24 hours. The data points represent the average percent of annexin V-positive, propidium iodide-negative cells (of the total cells counted) from triplicate experiments. The error bars represent the standard error of the means. FIG. 3B shows adherent HT-29 cells were treated with BAY 11-7085 at various concentrations for 24 hours after which the nonadherent and adherent cells were collected separately. The results shown are a graphic representation of individual flow cytometry results expressed as the percentage of cells that were annexin V-positive of those that excluded propidium iodide. FIG. 3C shows adherent HCT-116 cells were treated with 20 μM MG-132 for 24 hours after which the cells were collected. An immunoblot of the lysates for cleaved PARP was performed. Each lane represents equal total protein concentrations. FIG. 3D shows confluent monolayers of HT-29 cells were treated with various concentrations of BAY 11-7085 for 3 hours after which they were dispersed with trypsin-PBS. The cells were allowed to adhere to plastic dishes for 1 hour after which they were washed gently in PBS and stained with crystal violet. The crystal violet stained cells were solubilized in deoxycholate and the absorbance detected in a spectrophotometer at 590 nm. The adherent cells were expressed as a fraction of the controls Each data point represents the average of triplicate experiments and the error bars the standard errors of the means.

Figure 4A:
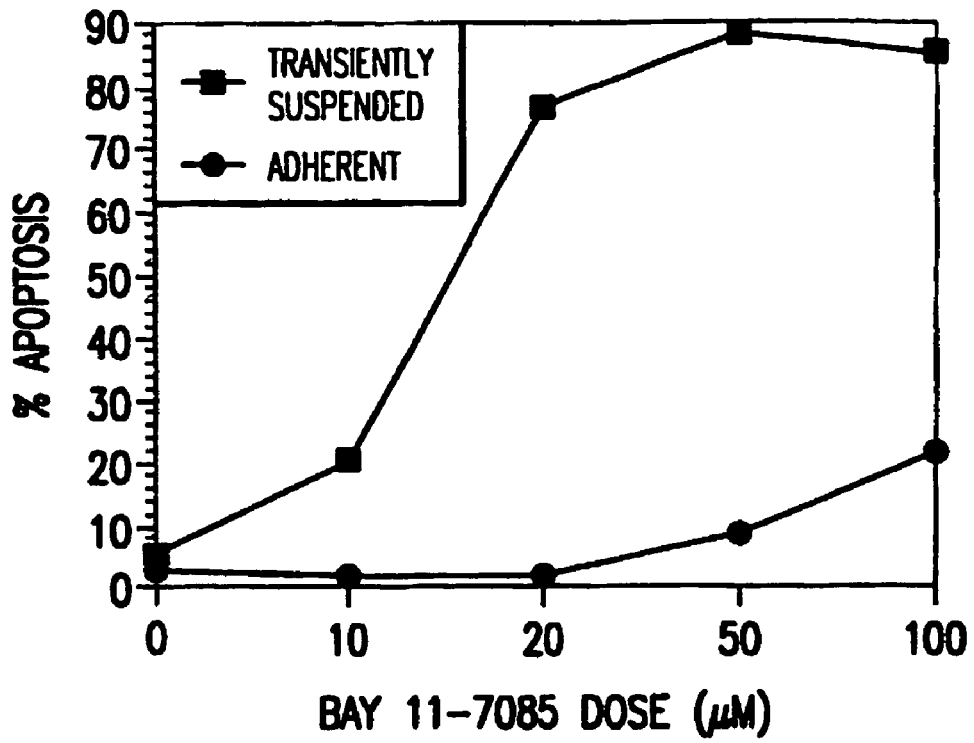
Figure 4B:
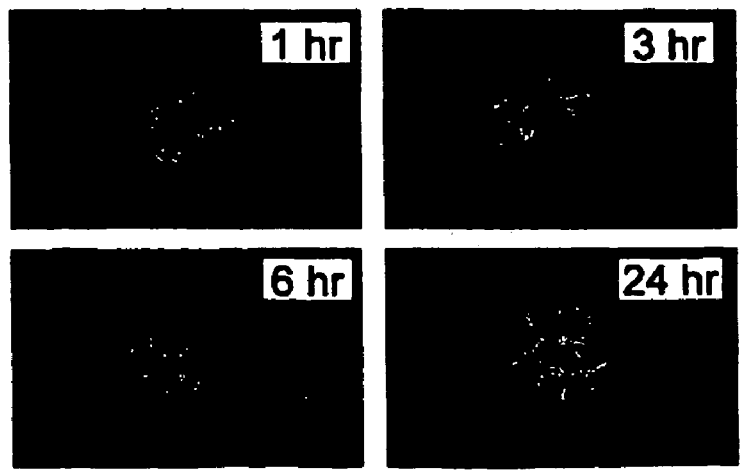
Figure 4C:
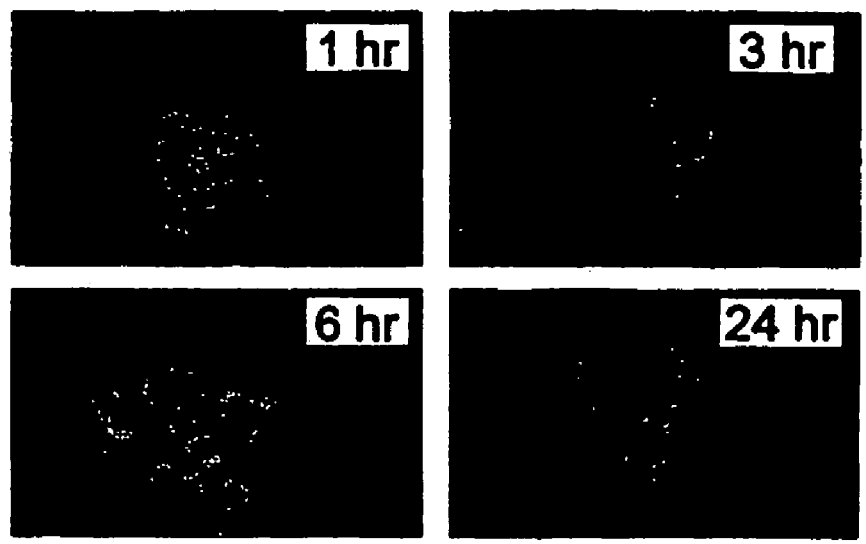
Figure 4D:
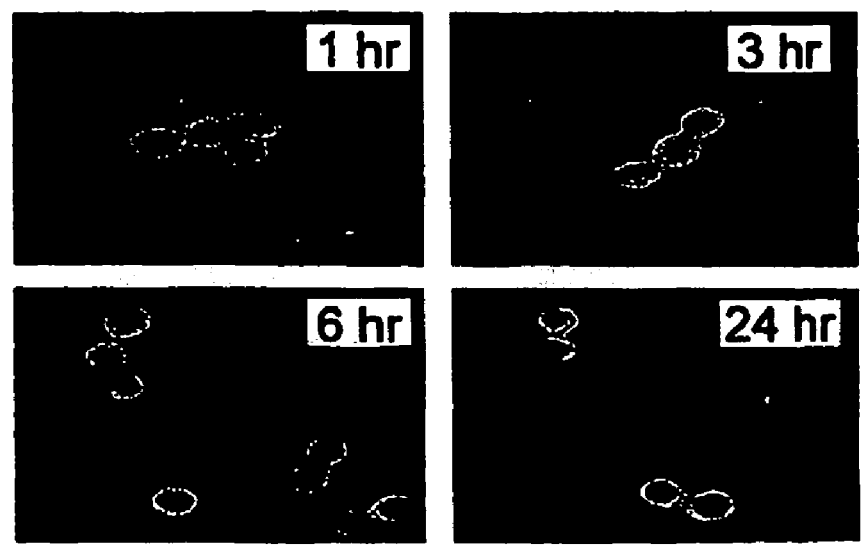

FIG. 4A shows transient suspension of colon cancer cells greatly increases their susceptibility to apoptosis in the presence of BAY 11-7085. HT-29 cells that were either transiently suspended with trypsin-EDTA or adherent for three days, were treated at time zero with DMSO or 10-100 μM BAY 11-7085. The percent of apoptotic cells was determined using the annexin V flow cytometry assay and graphed versus the dose of BAY 11-7085. FIG. 4B shows DLD-1, FIG. 4C shows HCT-116, and FIG. 4D shows HT-29 cells that were transiently suspended in trypsin-EDTA and allowed to readhere to glass coverslips for 1-24 hours. The cells were fixed and immunostained with an NF-κB p65 subunit monoclonal antibody. Note the strong nuclear staining at 1 hour versus the markedly reduced nuclear staining of the cells.

Figure 5A:
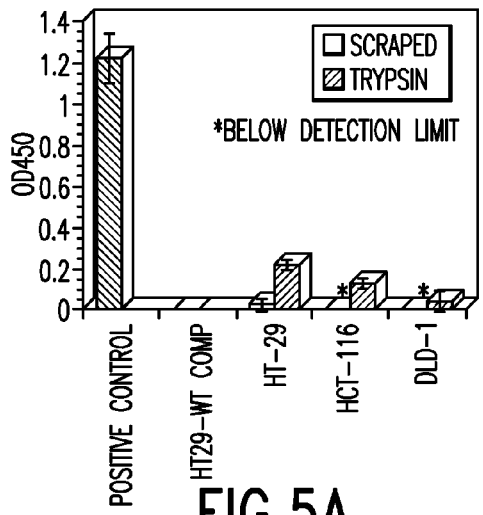
Figure 5B:
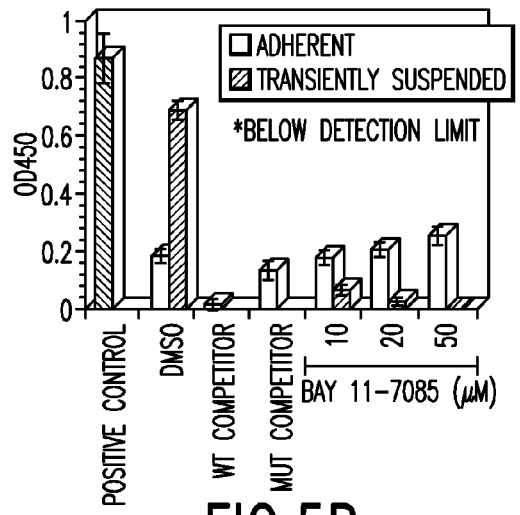
Figure 5C:
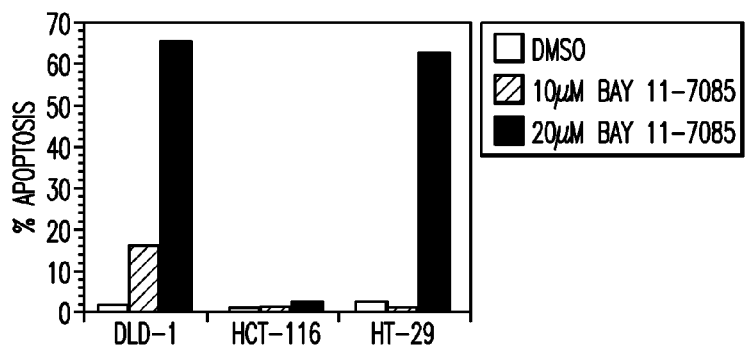
Figure 5E:
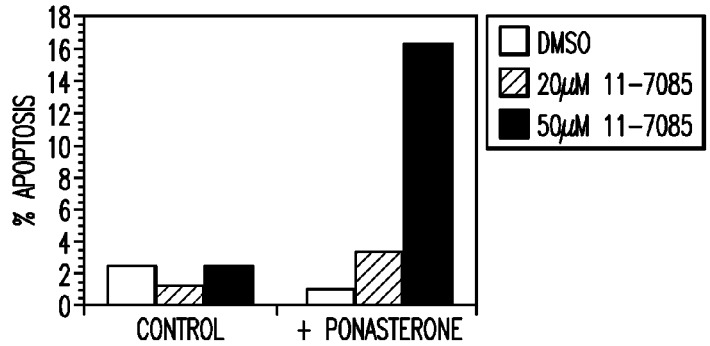
Figure 5D:
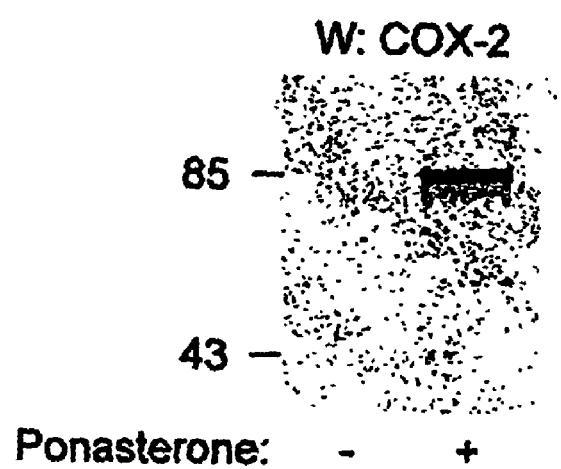

FIG. 5A shows NF-κB binding activity assay (TransAM) of DLD-1, HCT-116, and HT-29 cells that were transiently suspended by scraping or with trypsin-EDTA. The transiently suspended cells were lysed and allowed to bind to DNA oligonucleotides, containing the NF-κB consensus binding site, that were immobilized to 96-well plates. NF-κB protein bound to the oligonucleotides was detected by an antibody to the p65 subunit that only recognized p65 that is bound to DNA. The positive control was HeLa cells that were stimulated with TNFα A control was performed using excess free NF-κB oligonucleotides (Competitor). FIG. 5B shows HT-29 cells were transiently suspended and allowed to readhere in the presence or absence of BAY 11-7085 for three hours after which they were lysed. NF-κB binding activity was determined by the TransAM assay as in FIG. 5A. FIG. 5C shows transiently suspended DLD-1, HCT-116, and HT-29 cells were allowed to readhere in the presence of DMSO or BAY 11-7085 for 8 hours after which the percent of apoptotic cells was determined by the flow cytometric annexin V assay. The data shown represent typical results of three separate experiments. FIG. 5D shows 293-COX-2 cells were incubated in the presence or absence of 1 µg/ml of ponasterone for 48 hours after which they were lysed. An immunoblot for COX-2 was performed. FIG. 5E shows 293-COX-2 cells were incubated in the presence or absence of ponasterone for 48 hours followed by 8 hours of exposure to DMSO or BAY 11-7085. Note that induction of COX-2 resulted in an increased susceptibility to BAY 11-7085-induced apoptosis.

FIG. 6 shows an intraabdominal seeding model. FIGS. 6A, B, C show tumor implants of the liver of three athymic mice 21 days after receiving intraperitoneal injections of HT-29 cells. The mice were pretreated and treated for a total of 21 days with DMSO twice weekly. FIG. 6D shows intestinal tumor implants (arrows) of an athymic mouse 21 days after intraperitoneal injections of HT-29 cells. The mouse was pretreated and treated for a total of 21 days with DMSO twice weekly. FIG. 6E shows a micrograph showing tumor invasion through the liver capsule. This section was obtained from the tumor implant from the mouse in FIG. 6A. FIG. 6F shows a peritoneal tumor implant taken from the bowel wall of the mouse in FIG. 6A. FIG. 6G, (liver), FIG. 6H, (abdominal wall), and FIG. 6I, (intestinal) show tumor implants in three athymic mice 21 days after receiving intraabdominal injections of HCT-116 cells. All of the mice were treated with 5 mg/kg of BAY 11-7085 twice weekly.

FIG. 7A shows DLD-1 HCT-116, and HT-29 cells were cultured in 96-well plates for 10 days in the presence or absence of 10 or 50 µg/ml of cA2. At various time-points the cells were the cells were fixed, stained with crystal violet, solubilized in deoxycholate, and read in a spectrophotometer at 590 nm. The data points represent the means of triplicate experiments and the error bars the standard errors of the means. FIG. 7B shows adherent HT-29 cells were pretreated with 50 µg/ml of cA2 for 48 hours followed by the addition of DMSO or 20 µM BAY 11-7085 for another 24 hours. The percent of apoptotic cells was then determined by the annexin V assay. Similar results were obtained for DLD-1 cells. The results shown are typical of two separate experiments. FIG. 7C shows adherent or transiently suspended HT-29 cells were treated with 20 µM BAY 11-7085 for 8 hours after which they were lysed. Immunoblots were performed for c-IAP-2, TRAF-1, TRAF-2, and FLIP. All lanes contain equal total protein. FIG. 7D shows a FLIP immunoblot of DLD-1, HCT-116, and HT-29 lysates.

Figure 8:
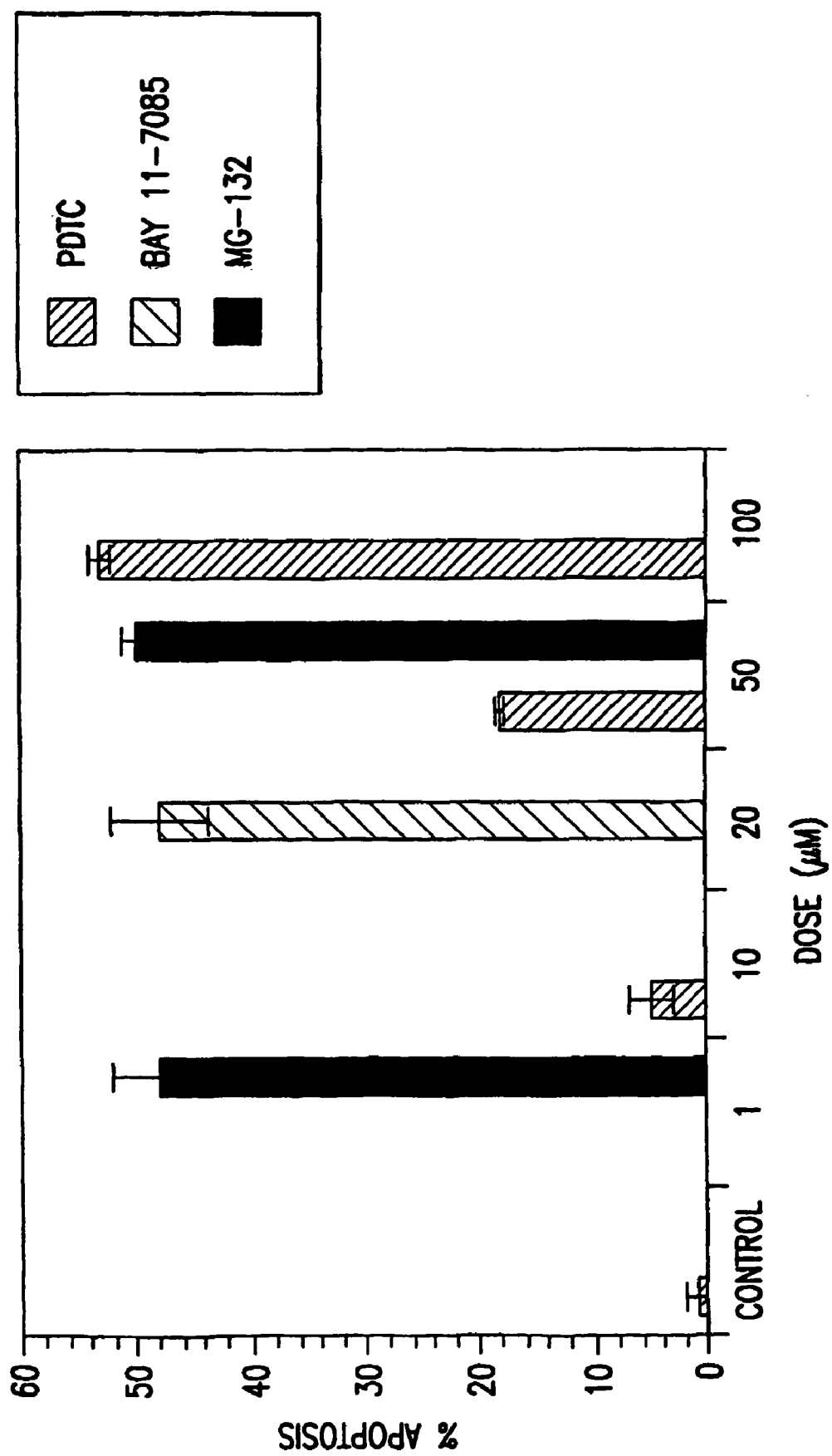

FIG. 8 shows HT-29 cells that were transiently suspended and allowed to readhere in the presence or absence of various concentrations of the NF$_\kappa$B inhibitors, PDTC, BAY 11-7085, and MG-132 for 4 h. The percentage of apoptotic cells was determined using the annexin V assay. The data points represent the averages of three experiments; bars, ±SE. E. DLD-1 and F. HT-29 cells were transduced with an adenovirus containing the I$_\kappa$B super-repressor construct. After 3 days, the cells were transiently suspended and allowed to readhere in the presence of subapoptotic concentrations of BAY 11-7085 or DMSO (vehicle) for 8 h. The data are expressed as fractions of cells surviving compared with the controls (no adenovirus) and were quantitatively determined by staining the remaining adherent cells with crystal violet.

IV. DETAILED DESCRIPTION

Before the present compounds, compositions, articles, devices, and/or methods are disclosed and described, it is to be understood that the disclosed compositions and methods are not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" as well as "less than" and "greater than" 10 are also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Variables such as $R_1$—$R_7$, X, and Y used throughout the application are the same variables as previously defined unless stated to the contrary.

In this specification and in the claims that follow, reference will be made to a number of terms that shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

The term "alkenyl" as used herein refers to a hydrocarbon group of 2 to 24 carbon atoms and structural formula containing a carbon-carbon double bond.

The term "alkynyl" as used herein refers to a hydrocarbon group of 2 to 24 carbon atoms and a structural formula containing a carbon-carbon triple bond.

The term "halogenated alkyl" as used herein refers to an alkyl group as defined above with one or more hydrogen atoms present on the alkyl groups substituted with a halogen (F, Cl, Br, I).

The term "aromatic" is defined as any carbon-based aromatic group including, but not limited to, benzene, naphthalene, etc. The term "aromatic" also includes "heteroaromatic," which is defined as an aromatic group that has at least one heteroatom incorporated within the ring of the aromatic group.

The term "substituted aromatic" is defined as an aromatic group having at least one group attached to the aromatic group that is not hydrogen. Examples of groups that can be attached to the aromatic group include, but are not limited to, alkyl, alkynyl, alkenyl, aryl, heterocyclic, halide, nitro, amino, ester, ketone, aldehyde, hydroxy, carboxylic acid, or alkoxy.

The term "aralkyl" is defined as an aryl group having an alkyl, alkynyl, or alkenyl group attached to the aromatic group. An example of an aralkyl group is a benzyl group.

B. Compositions and Methods

1. NF-κB

NF-κB is a heterodimeric transcription factor comprised of various protein subunits: p50/p105, p65/RelA, p52/p100, c-Rel, and RelB. NF-κB is localized to the cytoplasm by association with the IκB proteins, which inhibit translocation of NF-κB into the nucleus thus preventing its transcriptional activity. (Beg et al., 1992) Under the influence of cytokines, reactive oxygen species, growth factors, and other stimuli, IκB kinases (IKK) phosphorylate IκB proteins on two critical serine residues. (DiDonato et al., 1996; Traenckner et al., 1995) This then targets the IκB proteins for ubiquitination and subsequent degradation by the proteasome, which results in free NF-κB that translocates into the nucleus and activates the transcription of various genes possessing κB consensus DNA binding sites in their promoters. (Alkalay et al., 1995; Chen et al., 1995; Henkel et al., 1993). Many of the genes regulated by NF-κB encode proteins that promote inflammation, including COX-2, (Crofford et al., 1997; Newton et al., 1997a; Newton et al., 1997b; Schmedtje et al., 1997) and angiogenesis factors such as VEGF.(Huang et al., 2001). In addition, NF-κB mediates the transcription of several survival genes, c-Myc, Bcl2, p53, p21, c-FLIP, c-IAP-1, c-IAP-2, XIAP, IEX-1L COX-2, TRAF-1, and TRAF-2. (Kreuz et al., 2001; Schwartz et al., 1999; Stehlik et al., 1998; Wang et al., 1998; Wu et al., 1998).

Disclosed herein soluble NF-κB inhibitors inhibit anchorage-dependent and -independent proliferation, and tumorigenicity, and cause apoptosis of cancer cells including colon cancer cells. The induction of apoptosis of colon cancer cells by NF-κB inhibition occurs in a cell adhesion-dependent fashion. Readhesion following transient suspension of the cell lines causes a large activation of NF-κB, which rendered the cells exquisitely sensitive to NF-κB inhibitor-induced apoptosis. Furthermore, pretreatment of athymic mice with an NF-κB inhibitor completely prevented liver metastasis following intraperitoneal delivery of a colon cancer cell line. Disclosed herein colon cancer cells, as well as cancer cells related to colon cancer cells, utilize NF-κB for mitogenesis and as a major survival factor during readhesion.

2. NF-κB Inhibitors

The NF-κB inhibitors disclosed herein can be any molecule that inhibits NF-κB function. It is understood that NF-κB function can be inhibited or altered in many ways. For example, NF-κB function can be inhibited by the NF-κB inhibitor directly interacting with NF-κB. Directly interacting with NF-κB means that the inhibitor touches or binds with NF-κB. The NF-κB inhibitor can also indirectly inhibit NF-κB function. Indirectly inhibiting the function of NF-κB means that the NF-κB inhibitor does not touch or bind NF-κB. A molecule would indirectly inhibit NF-κB function, by for example, reducing the expression or activation or nuclear transport of NF-κB.

One example of indirect NF-κB inhibitors are NF-κB inhibitors that inhibit NF-κB transport into the nucleus. NF-κB remains cytoplasmic if it interacts with IκB. When IκB is phosphorylated, it causes IκB to be ubiquinated, and degraded, which allows NF-κB to transport to the nucleus. Disclosed are compositions which inhibit NF-κB transport to the nucleus through interactions with IκB which prevent IκB from interacting with NF-κB. One example of indirect NF-κB inhibitors that inhibit NF-κB transport into the nucleus are NF-κB inhibitors that inhibit IκB phosphorylation. Another example of indirect NF-κB inhibitors are NF-κB inhibitors that inhibit expression of NF-κB. Another example of indirect NF-κB inhibitors are NF-κB inhibitors that inhibit translation of NF-κB.

Typically the disclosed NF-κB inhibitors inhibit TNFα induced NF-κB activation. TNFα typically causes an activation of NF-κB. The disclosed inhibitors decrease this TNFα-induced activation. Many assays can be used to determine if NF-κB inhibitors are decreasing TNFα-dependent activation.

Disclosed are NF-κB inhibitors that can inhibit anchorage dependent and independent proliferation and tumorigenicity and can cause apoptosis. Also disclosed are NF-κB inhibitors that inhibit induction of apoptosis by NF-κB inhibition which occurs in a cell adhesion dependent fashion. Disclosed are NF-κB inhibitors that affect cells where readhesion of cells causes a large activation of NF-κB which causes the cells to become sensitized to NF-κB inhibitor induced apoptosis.

Disclosed herein are colon cancer cells, as well as other cancer cells, which utilize NF-κB for mitogenesis and are a survival factor during readhesion. Disclosed is that NF-κB inhibitors diminish colon cancer cell proliferation.

BAY 11-7082 and BAY 11-7085 inhibit IκB phosphorylation and TNFα induced NF-κB activation. Disclosed herein, BAY 11-7082 inhibits growth of DLD-1 and HCT-116 cancer cell lines.

Disclosed herein NF-κB inhibitors inhibit colon cancer cell tumorigenicity.

Disclosed herein, cells that contain APC mutations are susceptible to BAY 11-7085 and related molecules. For example, cells obtained from cell lines DLD-2 and HT-29 cells are susceptible to BAY 11-7085. DLD-1 and HT-29 contain APC mutations. HCT-116 cells have activating mutations on B-catenin which is normally regulated by the APC product. Also HCT-116 cells do not express COX-2. COX-2 is commonly over-expressed in colorectal cancers, but HCT-116 cells do not.

Disclosed herein anchorage independent inhibition of proliferation is inhibited by both BAY11-7082 and 7085 in DLD-1 and HT-29 cells, and both BAY 11-/082 and BAY 11-7085 reduce tumor volumes in vivo in athymic mice injected with HT-29 tumor cells.

Disclosed herein MC-132 and PDTC cause an increase in apoptosis in adhered cells and BAY-11-7085 and BAY-11-7082 cause apoptosis in cells even when not adhered.

C. Methods of Using the Compositions

The disclosed compositions can be used in a variety of ways as research tools. For example, the disclosed compositions, such as BAY-11-7085 and BAY-11-7082, PDTC and MC-132 can be used as reagents and standards in cellular proliferation assays and as NF-κB inhibitors for assays related to cancer.

The compositions can be used for example as competitive inhibitors in combinatorial chemistry protocols or other screening protocols to isolate molecules that possess desired functional properties related to inhibition of cancer or metastasis of cell systems disclosed herein.

1. Method of Treating Cancer

Disclosed herein NF-κB inhibitors can be given to a subject. Any subject in need of the NF-κB inhibitors as disclosed herein can be given the NF-κB inhibitors. The subject can, for example, be a mammal, such as a mouse, rat, rabbit hamster, dog, cat, pig, cow, sheep, goat, horse, or primate, such as monkey, gorilla, orangutan, chimpanzee, or human.

Disclosed herein NF-κB inhibitors can be used for inhibiting cancer cell proliferation. Inhibiting cancer cell proliferation means reducing or preventing cancer cell growth. Inhibitors can be determined by using a cancer cell assay. For example, either a DLD-1, HCT-116, and HT-29 cell line can be cultured on 96-well plates in the presence or absence of the inhibitor for 8 days. The cells can be fixed, stained with crystal violet, solubilized in deoxycholate, and read in a spectrophotometer at 590 nm. In certain embodiments the inhibitors are those that will inhibit 10% or 15% or 20% or 25% or 30% or 35% or 40% or 45% or 50% or 55% or 60% or 65% or 70% or 75% or 80% or 85% or 90% or 95% of the cell growth relative to a control as determined by spectrophotometry.

In certain embodiments the inhibitors also inhibit anchorage-dependent proliferation of cancer cells, such as colon cancer cells. Inhibitors can be assayed using a soft agar colony formation assay. For example, DLD-1, HCT-116, and HT-29 cells can be cultured for 6 days in soft agar in the presence of DMSO (control) or inhibitor. The number of colony counts can then be compared by, for example, taking a percentage of the cells formed relative to a control. In certain embodiments the inhibitors are those that will inhibit 10% or 15% or 20% or 25% or 30% or 35% or 40% or 45% or 50% or 55% or 60% or 65% or 70% or 75% or 80% or 85% or 90% or 95% of the cell growth relative to a control as determined by counting colonies formed.

Disclosed herein NF-κB inhibitors can be used for promoting cancer cell apoptosis. Promoting cancer cell apoptosis means causing the cell to die. An apoptosis assay can be used to determine if the inhibitors promote cancer cell apoptosis. For example, an apoptosis assay as disclosed in Example 1 can be used. In certain embodiments, the percent of apoptosis was determined as the percent of annexin V-positive, propidium iodide-negative cells of the total cells counted in an Apoptosis assay, such as that disclosed in Example 1. In certain embodiments, the inhibitor causes at least 10% of the cells to be apoptotic or the inhibitor causes at least 15% of the cells to be apoptotic or the inhibitor causes at least 20% of the cells to be apoptotic or the inhibitor causes at least 25% of the cells to be apoptotic or the inhibitor causes at least 30% of the cells to be apoptotic or the inhibitor causes at least 35% of the cells to be apoptotic or the inhibitor causes at least 40% of the cells to be apoptotic or the inhibitor causes at least 45% of the cells to be apoptotic or the inhibitor causes at least 50% of the cells to be apoptotic or the inhibitor causes at least 55% of the cells to be apoptotic or the inhibitor causes at least 60% of the cells to be apoptotic or the inhibitor causes at least 65% of the cells to be apoptotic or the inhibitor causes at least 70% of the cells to be apoptotic or the inhibitor causes at least 75% of the cells to be apoptotic or the inhibitor causes at least 80% of the cells to be apoptotic or the inhibitor causes at least 85% of the cells to be apoptotic or the inhibitor causes at least 90% of the cells to be apoptotic or the inhibitor causes at least 95% of the cells to be apoptotic.

In certain embodiments, the apoptotic effect of the disclosed inhibitors is enhanced in cells that are transiently suspended, such as metastatic cells circulating through the blood stream, prior to readhesion. Inhibitors that have this property can be determined by assaying their apoptotic effect as, for example described herein, in a transient suspension assay, as for example described in Examples 1 and 2. For example, cells can be put into suspension by scraping and then allowed to readhere. Inhibitors that cause an increase in apoptosis upon readhering to the substrate are disclosed. An increase upon readhering to the substrate can be determined by, for example, looking at multiples of cells that were apoptotic upon readhering to the substrate compared with cells that were apoptotic upon remaining in suspension. Disclosed are inhibitors wherein the inhibitor causes at least 1.5 fold or 2 fold or 3 fold or 4 fold or 5 fold or 6 fold or 7 fold or 10 fold or 15 fold or 20 fold or 30 fold or 50 fold or 100 fold more apoptosis of cells that readhere then apoptosis of cells that remain in suspension. (see for example FIG. 3).

In certain embodiments, the inhibitor causes at least 17% of the cells to be apoptotic.

Disclosed herein NF-κB inhibitors can be used for inhibiting readhesion of cancer cells to a surface. Inhibiting readhesion of cancer cells to a surface means decreasing the number of cells capable of readhering to a surface after being transiently suspended as discussed herein.

Disclosed herein NF-κB inhibitors can be used for inhibiting metastasis of cancer cells. Inhibiting metastasis of cancer cells means decreasing or lowering the amount of metastatic tumors that arise in an organism. For example, disclosed are inhibitors that inhibit metastasis in an in vivo assay. One way of performing an in vivo assay to determine if an inhibitor inhibits metastasis is to inject a cancer cell line, such as HT-29, into the abdominal cavity of an athymic mouse. Mice are pretreated with the inhibitor or a control intraperotneally, for example. The mouse can then be treated regularly, for example, twice weekly with vehicle or BAY 11-7085 for a period of time, for example, 21 days. The mouse can then be sacrificed and assayed for metastatic tumor formation. Disclosed are compositions which inhibit metastatic tumor formation in this type of assay disclosed herein, as well as compositions that reduce metastatic tumor formation by at least 10% or 15% or 20% or 25% or 30% or 35% or 40% or 45% or 50% or 55% or 60% or 65% or 70% or 75% or 80% or 85% or 90% or 95% relative to a control compound.

For example, NF-κB inhibitors can inhibit intraabdominal metastasis arising from, for example, colon or rectal cancers. NF-κB inhibitors can also inhibit hepatic, parietal or peritoneal metastasis arising from, for example, colon or rectal cancers.

Disclosed herein NF-κB inhibitors can be used for inhibiting tumorigenesis. Inhibiting tumorigenesis means decreasing or lowering the amount of tumors present in an organism. For example, disclosed are inhibitors that inhibit tumorigenesis in an in vivo assay. One way of performing an in vivo assay to determine if an inhibitor inhibits tumorigenesis is to inject a cancer cell line subcutaneously, such as HT-29, into an athymic mouse, such as a female mouse. The mouse can then be treated regularly, for example, twice weekly with vehicle or BAY 11-7085 for a period of time, for example, 21 days or 28 days. The mouse can then be sacrificed and assayed for tumor formation and size. Disclosed are compositions which inhibit tumorigenesis in this type of assay disclosed herein, as well as compositions that reduce tumorigenesis by at least 10% or 15% or 20% or 25% or 30% or 35% or 40% or 45% or 50% or 55% or 60% or 65% or 70% or 75% or 80% or 85% or 90% or 95% relative to a control compound.

Disclosed herein NF-κB inhibitors can be administered to cells that utilize NF-κB for mitogenesis. Disclosed herein NF-κB inhibitors can be administered to cells that utilize NF-κB for readhesion. A cell can be determined to utilize NF-κB for readhesion if in a transient suspension assay, upon readhesion NF-κB is activated as determined by any assay that looks at NF-κB activation. For example, NF-κB binding assays to the consensus sequence can be used, such as Trans-AM® assay the discussed in Examples 1 and 2. If the NF-κB activation is greater upon readhesion then in suspension, the cells can be considered to utilize NF-κB for readhesion.

Disclosed herein NF-κB inhibitors can be administered to cells to induce the apoptosis of the cells in a TNFα independent manner. TNFα can activate apoptosis, but the NF-κB inhibitors can be administered to cause apoptosis in a TNFα independent manner. The disclosed inhibitors can promote apoptosis of cancer cells, such as colon cancer cells, without TNFα. An inhibitor or cell can be shown to be apoptotic without needing the inhibitor by using TNFα inhibiting antibody, such as cA2, and seeing that apoptosis is still caused by the inhibitor even in the presence of the TNFα inhibiting antibody, such as cA2.

When the NF-κB inhibitors are administered, they typically cause a decrease in the expression of anti-apoptotic proteins. Expression of the anti-apoptotic proteins can be determined by any means for determining expression. For example, standard biotechnology methods such as PCR or Northern blots can be used to determine the expression levels of anti-apoptotic genes. A decrease can be determined by assaying the expression levels of a desired anti-apoptotic gene in the presence of a potential inhibitor and comparing this level of expression to the level of expression in the absence of the inhibitor. Disclosed are inhibitors, which decrease the expression of the anti-apoptotic genes in such an assay.

As discussed herein NF-κB inhibitors can, for example, be used to reduce the proliferation of cancer cells, as well as to cause the apoptosis of cancer cells or inhibit the readhesion of cancer cells or inhibit the metastasis of cancer cells. NF-κB inhibitors can, for example, be administered to any cancer cell that uses NF-κB to survive or metastize or adhere or which activates NF-κB during its life cycle.

NF-κB inhibitors can be administered to cancer cells that have a mutation in the adenomatous polyposis coli (APC) gene. APC has been shown to be a tumor suppressor gene in, for example, colon cells (see for example, Groden et al., Cancer Research, 55 1531-1539 (1995) herein incorporated by reference at least for material related to APC mutations and assays of the same). A variety of different morphologies of the effect of the mutated APC can be seen. Whether a cell contains an APC mutation can be assayed for using standard recombinant biotechnology protocols, for example, sequencing and PCR analysis or ligation mediated chain reaction (LCR) or other methods using (for example chip technology) capable of assaying and comparing DNA sequences. The mutations can readily be assayed as being functional mutations, by for example, expressing the mutant protein in a cell and determining if the mutant protein induces an oncogenic phenotype. Assays for determining the effect of an APC mutation can also be performed as discussed in Groden et al. In certain embodiments an activating mutation can be determined by assaying the mutation and comparing the effects to the effects of APC mutations in DLD-1 cells or HT29 cells. For example, as in Groden a fully functional APC gene can be transfected into a DLD-1 or HT29 cell, and this decreases the oncogenic behavior of the DLD-1 or HT29 cells because the non-mutant APC gene rescues normal phenotype. In certain embodiments, a given APC mutation can be assayed by, for example, transfecting the mutant APC into either a DLD-1 or HT29 cell line and comparing the level of rescue provided by the mutant APC to the level of rescue of the non-mutant APC. In certain embodiments the APC mutant will be considered an in-activating APC mutant, i.e. a mutant which causes oncogenic phenotype, if the rescue of the cells transfected by the mutant APC is less than 10% or 15% or 20% or 25% or 30% or 35% or 40% or 45% or 50% or 55% or 60% or 65% or 70% or 75% or 80% or 85% or 90% or 95% of the rescue of cells transfected with the non-mutant APC, as judged by any of the criteria used to judge oncogenic phenotype of DLD-1 or HT29 cells.

In certain embodiments, NF-κB inhibitors are not administered to cancer cells that have an activating mutation on β-catenin. Whether a cell contains a β-catenin mutation can be assayed for using standard recombinant biotechnology protocols, for example, sequencing and PCR analysis. The mutations can be assayed for function as discussed herein.

Disclosed herein NF-κB inhibitors can be administered to cancer cells that express the COX-2 gene. A cell expresses the COX-2 gene if there are detectable transcripts of the COX-2 gene in the cell using an assay to detect transcripts, such as a hybridization assay, such as a northern blot or any of the chip type assays available, or an amplification based assay based on, for example, PCR or other amplification methods. In certain embodiments, the NF-κB inhibitors can be administered to cancer cells that over express the COX-2 gene. Over expression of COX-2 can be determined by using any of the methods and assays discussed for the expression of COX-2 and comparing the level of expression to that of a control population of cells. In general cells do not show activated COX-2 expression, even if there is a basal amount of COX-2 expression, but upon additions of mitogens, for example, COX-2 expression, relative to expression in the absence of mitogens, increases. Thus, a give cancer cell or cancer cell line can be assayed for COX-2 expression and this can be compared to the COX-2 expression of this cell type in the absence of the oncogenic phenotype. In certain embodiments a given cancer cell line can be considered to over express COX-2 if the expression is at least 10% or 15% or 20% or 25% or 30% or 35% or 40% or 45% or 50% or 55% or 60% or 65% or 70% or 75% or 80% or 85% or 90% or 95% of the expression of COX-2 in DLD-1 cells or HT29 cells, when expression of COX-2 of the cell of interest and DLD-1 or HT29 are assayed in parallel.

Disclosed herein NF-κB inhibitors can be administered to cancer cells that express the COX-2 gene as well as having mutations in the APC gene.

It is understood that certain cancers can give rise to cancer cell lines. Typically a cancer cell line are cells that are maintained in cell culture, but that arose from a specific type of cancer. NF-κB inhibitors can be used for a variety of cancers, but can, for example, be used for cancers that are related to the DLD-1 cancer cell line and the HT-29 cancer cell line. The DLD-1 cancer cell line and the HT-29 cancer cell line, arose from colon cancer cells. Also disclosed are cancer cell lines having the properties of the DLD-1 cancer cell line and the HT29 cell line.

The disclosed compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, stomach cancer, head and neck carcinoma, large bowel cancer, hematopoietic cancers; testicular cancer, colon and rectal cancers, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

As disclosed herein, the NF-κB inhibitors prevent readhesion of transiently suspended cancer cells, for example, colon cancer cells, and for example, cancer cells related to HT29 and DLD1 cell lines. Also, it is well understood that during surgery to remove solid tumors, as discussed herein, cancer cells can break of and become transiently suspended in the subject's circulatory system, only to potentially readhere at a new spot, to seed a new tumor growth. This reseeding occurs during metastasis as well, but can be accelerated during surgical resection of the tumor. Thus, the disclosed NF-κB inhibitors can be used to prevent or inhibit the potential reseeding that can occur during or after surgical resection of a tumor. By administering the NF-κB inhibitors prior to or after the resection, the transiently suspended cells can be efficiently caused to apoptos with the NF-κB inhibitors.

Thus disclosed are methods of inhibiting cancer cell proliferation in a subject comprising administering an NF-κB inhibitor to the subject, wherein the subject has had a tumor resected.

Also disclosed are methods, wherein the NF-κB inhibitor is administered prior to the resection or after the resection or both.

Disclosed are methods, wherein the NF-κB inhibitor is administered within 10 days or 5 days or 1 day or 10 hours or 5 hours or 1 hour or 0.5 hours, of the resection.

D. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular composition such as BAY 11-7082 is disclosed and discussed and a number of modifications that can be made to a number of molecules including BAY 11-7082 are discussed, specifically contemplated is each and every combination and permutation of BAY 11-7082 and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. NF-κB Inhibitors

The disclosed method involve NF-κB inhibitors. An NF-κB inhibitor can be any composition that causes a decrease in the expression of anti-apoptotic proteins. The NF-κB inhibitor can also be any composition wherein the composition inhibits IκB phosphorylation. The NF-κB inhibitor can also be any composition, wherein the composition inhibits TNFα induced NF-κB activation.

In certain embodiments, the inhibitors useful in any of the methods are olefins. An "olefin" is defined herein as any compound or molecule possessing at least one carbon-carbon double bond. Each carbon atom of the carbon-carbon double bond may be unsubstituted or independently substituted with one or two different moieties.

In certain embodiments, the inhibitor is an olefin having at least one electron-withdrawing group. In another embodiment, the inhibitor is an olefin having at least two electron-withdrawing groups. In this case, when two electron-withdrawing groups are present, the electron-withdrawing groups can be present on the same olefinic carbon atom or one electron-withdrawing group can be on each olefinic carbon atom.

The term "electron-withdrawing group" is any group that has an affinity or attraction for electron density. For example, when an electron-withdrawing group is attached to an olefinic carbon atom ($C_\alpha$), then the other olefinic carbon atom ($C_\beta$) is more susceptible to nucleophilic attack (i.e., $C_\beta$ is more electropositive) when compared to an olefin that does not possess an electron-withdrawing group. Generally, electron withdrawing groups possess one or more carbon-carbon multiple bonds, carbon-heteroatom multiple bonds, or heteroatom-heteroatom multiple bonds. Examples of electron-withdrawing groups include, but are not limited to, a cyano group, a sulfo-oxy group, a phospho-oxy group, a carboxyl group, a nitro group, a halogen, a halogenated alkyl group, an unsubstituted aromatic ring, or a substituted aromatic ring having at least one cyano group, sulfo-oxy group, phospho-oxy group, carboxyl group, hydroxyl group, amino group, ether group, halogenated alkyl group, halogen, or nitro group.

The term "phospho-oxy group" is a group having one of the following structures

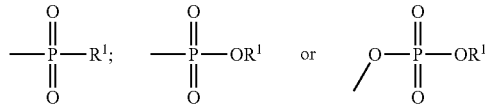

wherein $R^1$ is hydrogen, alkyl, halogenated alkyl, alkenyl, alkynyl, aralkyl, or substituted or unsubstituted aromatic.

The term "sulfo-oxy group" is a group having one of the following structures

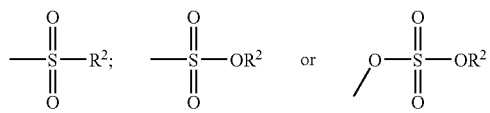

wherein $R^2$ is hydrogen, alkyl, halogenated alkyl, alkenyl, alkynyl, aralkyl, or substituted or unsubstituted aromatic. In one embodiment, the inhibitor is an olefin having a cyano group and a sulfo-oxy group having the structure

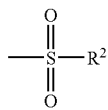

wherein $R^2$ is hydrogen, alkyl, halogenated alkyl, alkenyl, alkynyl, aralkyl, or substituted or unsubstituted aromatic.

In another embodiment, the inhibitor has the structure I.

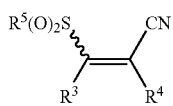

wherein $R^3$, $R^4$ and $R^5$ are, independently, hydrogen, alkyl, halogenated alkyl, alkenyl, alkynyl, aralkyl, or substituted or unsubstituted aromatic, wherein the compound is the E- or Z-isomer. The stereochemistry about the carbon-carbon double bond will vary depending upon the relative positions of the cyano group (—CN) and the sulfonyl group (—S(O$_2$)R$^5$)). When the cyano group and sulfonyl group are, cis to one another, then the compound is the Z-isomer, and when the cyano group and sulfonyl group are trans to one another, then the compound is the E-isomer. In one embodiment, the inhibitor having the structure I is the E-isomer.

In one embodiment, when the inhibitor has the structure I, $R^3$ and $R^4$ are hydrogen. In another embodiment, $R^5$ is methyl, ethyl, propyl, isopropyl, butyl, isobutyl, tertiary butyl, substituted or unsubstituted phenyl, or benzyl. In a further embodiment, $R^5$ is a phenyl group having at least one alkyl group.

In another embodiment, the inhibitor having the structure I is the ethyl ester of 2-cyano-3-(methylsulfonyl)-3-(1,2,4,5-tetrahydro-3H-3-benzazepin-3-yl-2-propenoic acid; (2,2-bis[p-(dimethylamino)phenyl]vinyl](methylsulfonyl)-fumaronitrile; [2,2-bis[p-dimethylamino)phenyl]vinyl](hydroxymethyl)sulfonyl)-fumaronitrile, p-toluenesulfonate; [2,2-bis[p-dimethylamino)phenyl]vinyl](ethylsulfonyl)-fumaronitrile; (benzylsulfonyl) [2,2-bis[p-(dimethylamino)phenyl]vinyl]-fumaronitrile; (allylsulfonyl) [2,2-bis[p-dimethylamino)phenyl]vinyl]-fumaronitrile; benzyl(benzylsulfonyl)-fumaronitrile; 1,7-bis(allylsulfonyl)-4-hydroxy-1,3,5-Heptatriene-1,2,6,7-tetracarbonitrile; 2-cyano-3-(methylsulfonyl)-3-(1,2,4,5-tetrahydro-3H-3-benzazepin-3-yl)-2-propenoic acid ethyl ester; alpha-[[[(1E)-1-cyano-2-(3,4-dihydroxyphenyl)ethenyl]sulfonyl]methylene]-3,4-dihydroxy-beta-oxo-(alpha E)-benzenepropanenitrile; 3-(methylsulfonyl)-(2E)-2-propenenitrile; 4,4,4-trifluoro-3-(hexylsulfonyl)-(2Z)-2-butenenitrile; alpha-[[[1-cyano-3-(3,4-dihydroxyphenyl)-3-oxo-1-propenyl]sulfonyl]methylene]-3,4-dihydroxy-(E,E)-benzeneacetonitrile; 2,2'-[1,3-propanediylbis[(cyclohexylimino)4,1-phenylene]]bis[3-(ethylsulfonyl)-2-butenedinitrile; alpha-(methylsulfonyl)methylene)-(Z)-benzeneacetonitrile; alpha-[[(1,1-dimethylethyl)sulfonyl]methylene]-(Z)-benzeneacetonitrile; alpha-[methylsulfonyl)methylene]-(E)-benzeneacetonitrile; alpha-[[(phenylmethyl)sulfonyl]methylene]-benzeneacetonitrile; alpha-[(butylsulfonyl)methylene]-(E)-benzeneacetonitrile; alpha-[(butylsulfonyl)methylene)-(Z)-benzeneacetonitrile; alpha-[[(1-methylethyl)sulfonyl]methylene]-(E)-benzeneacetonitrile; alpha-[[(1-methylethy)sulfonyl]methylene]-(Z)-benzeneacetonitrile; alpha-[[(1,1-dimethylethyl)sulfonyl]methylene]-(E)-benzeneacetonitrile; alpha-[[[4-chlorophenyl)methyl]sulfonyl]methylene]-(E)-benzeneacetonitrile; alpha-[[[4-chlorophenyl)methyl]sulfonyl]methylene]-(Z)-benzeneacetonitrile; alpha-[[3-chloropropyl)sulfonyl]methylene]-(E)-benzeneacetonitrile; alpha-[[3-chloropropyl)sulfonyl]methylene]-(Z)-benzeneacetonitrile; 3-(methylsulfonyl)-(2E)-2-propenenitrile; 3-(methylsulfonyl)-(Z)-2-propenenitrile; alpha-[(methylsulfonyl)methylene]-2-nitro-benzeneacetonitrile; 4-(dimethylamino)-alpha-[[(trifluoromethyl)sulfonyl]methylene]-benzeneacetonitrile; 2-chloro-3-(methylsulfonyl)-2-propenenitrile; 2,3-dichloro-3-(methylsulfonyl)-2-propenenitrile; 2,3-dichloro-3-[(1-methylethyl)sulfonyl]-2-propenenitrile; 2,3-dichloro-3-[(1-methylpropyl)sulfonyl]-2-propenenitrile; 2,3-dichloro-3-[(3-methylbutyl)sulfonyl]-2-propenenitrile; 2,3-dichloro-3-(octylsulfonyl)-2-propenenitrile; 2,3-dichloro-3-(nonylsulfonyl)-2-propenenitrile; 3-[(2-phenylethenyl)sulfonyl]-2-propenenitrile; 3-[(2-phenylethenyl)sulfony1]-2-propenenitrile; alpha-[methylsulfonyl)phenylmethylene]-(Z)-benzeneacetonitrile; 3-(benzylsulfonyl)-acrylonitrile; 3-(methylsulfonyl)-2-propenenitrile; 3-(ethylsulfonyl)-acrylonitrile; 3,3'-(tetramethylenedisulfonyl)di-acrylonitrile; 3-[(2-cyanovinyl)sulfonyl)-propionitrile; 3-((4-(2,2-dichloro-1,1-difluoroethoxy)phenyl)sulfonyl)-2-propenenitrile; 3-((4-(2,2-dichloro-1,1-difluoroethoxy)-2-methyl-5-nitropheny)sulfonyl)-2-propenenitrile; or 3-((3-trifluoromethyl)phenyl)sulfonyl)-2-propenenitrile.

In another embodiment, the inhibitor is (2E)-3-(tolysulfonyl)-2-propenenitrile, which is also referred to as BAY-7082.

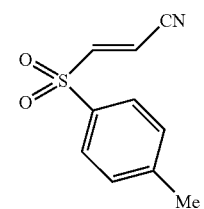

In another embodiment, the inhibitor is (2E)-3-[4-(tertiary butyl phenyl)sulfonyl]-2-propenenitrile, which is also referred to as BAY-11-7085.

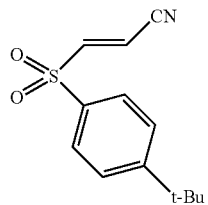

In an alternative embodiment, the inhibitors useful in any of the methods comprise at least one amino acid residue. An "amino acid residue" is produced when an amino acid is reacted with one or more compounds capable of reacting with the amino acid. For example, when an amino acid is reacted with two other amino acids to produce a tripeptide, the resultant tripeptide contains three amino acid residues. Alternatively, the amino acid can react with other non-amino acids to produce a compound having an amino acid residue.

In one embodiment, the inhibitor has at least one leucine residue. In another embodiment, the inhibitor comprises three leucine residues. In a further embodiment, the compound is N-[(phenylmethoxy)carbonyl]-L-leucyl-N-[(1S)-1-formyl-3-methylbutyl]-L-leucinamide, which has the structure

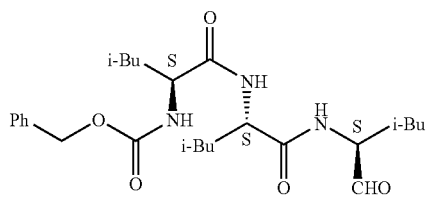

This compound is also referred to as Sigma MG-132.

In another embodiment, the inhibitor is pyrrolidine dithiocarbamate, which has the structure II

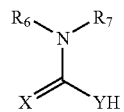

wherein $R_6$ and $R_7$ are, independently, hydrogen, alkyl, alkenyl, alkynyl, aralkyl, or substituted or unsubstituted aromatic, or $R_6$ and $R_7$ together form a ring with the nitrogen atom, and X and Y are, independently, oxygen or sulfur, or the pharmaceutically-accpetable salt, ester, or amide thereof.

In one embodiment, X and Y are both oxygen. In another embodiment, X and Y are both sulfur. In a further embodiment, $R_6$ and $R_7$ can form a ring system. For example, $R_6$ and $R_7$ can be collectively a methylene group such as $(CH_2)_3$. The resultant ring structure would be a four-membered ring with one nitrogen atom. When $R_6$ and $R_7$ form a ring, the ring can be from a three- to 10-membered ring. In one embodiment, X and Y are sulfur, and $R_6$ and $R_7$ is $(CH_2)_4$. This compound is also referred to herein as PDTC.

Formula II also enompasses pharmaceutically acceptable esters, amides, and salts of such compounds. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula II to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —$(CO)NH_2$, —$(CO)NHR$ and —$(CO)NR_2$, where R is an alkyl group defined above, can be prepared by reaction of the carboxylic acid-containing compound with ammonia or a substituted amine.

a) Direct Inhibitors

Disclosed are inhibitors which are direct inhibitors of NF-κB. A direct inhibitor of NF-κB is an inhibitor that interacts with NF-κB. A direct inhibitor touches in some way the NF-κB molecule such that the NF-κB dependent activities, such as readhesion and metastasis are inhibited.

b) Indirect Inhibitors

Disclosed are inhibitors which are indirect inhibitors of NF-κB. An indirect inhibitor of NF-κB is an inhibitor that does not interact with NF-κB. An indirect inhibitor touches in some way a molecule that is involved in a signal transduction pathway that NF-κB is involved in such that the NF-κB dependent activities, such as readhesion and metastasis are inhibited.

One example of an indirect inhibitor of NF-κB would be an indirect inhibitor which inhibits the expression of NF-κB and thereby prevent NF-κB from functioning. Another example of an indirect inhibitor of NF-κB would be an indirect inhibitor that inhibits translation of a gene encoding NF-κB.

An example of a molecule that is involved in a signal transduction pathway that NF-κB is involved in is IκB. Molecules that inhibit IκB from phosphorylating can be indirect inhibitors.

2. Homology/Identity

It is understood that one way to define any known variants and derivatives or those that might arise, of the disclosed genes and proteins herein is through defining the variants and derivatives in terms of homology to specific known sequences. For example, the sequences of a particular human NF-κB and IκB are known and readily obtainable at for example, a sequence database such as Genbank. The nucleic acids that encode these proteins are also readily available. These sequences and any known alleles or species variants are considered disclosed herein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

3. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

4. Nucleic Acids

There are a variety of molecules disclosed herein that are nucleic acid based, including for example the nucleic acids that encode, for example NF-κB or IκB, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989,86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to for example, the NF-κB or IκB genes, found in sequence data bases, such as Genbank. These sequences and others are herein incorporated by reference in their entireties as well as for individual subsequences contained therein.

Those of skill in the art understand how to resolve sequence discrepancies and differences and to adjust the compositions and methods relating to a particular sequence to other related sequences (i.e. sequences of NF-κB or IκB). Primers and/or probes can be designed for any NF-κB or IκB sequence given the information disclosed herein and known in the art.

c) Primers and Probes

Disclosed are compositions including primers and probes, which are capable of interacting with, for example, the NF-κB or IκB nucleic acids, such as mRNA, as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with, for example, the NF-κB nucleic acid, such as mRNA, or the IκB nucleic acid, such as mRNA, or region of the NF-κB or IκB nucleic acids or they hybridize with the complement of the NF-κB or IκB nucleic acids or complement of a region of the NF-κB or IκB nucleic acids.

d) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of NF-κB or IκB or the genomic DNA of NF-κB or IκB or they can interact with the polypeptide of NF-κB or IκB. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Both of these recognition motifs can also occur in the same functional nucleic acid molecule.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than $10^{-6}$. It is more preferred that antisense molecules bind with a $k_d$ less than $10^{-8}$. It is also more preferred that the antisense molecules bind the target molecule with a $k_d$ less than $10^{-10}$. It is also preferred that the antisense molecules bind the target molecule with a $k_d$ less than $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$. It is more preferred that the aptamers bind the target molecule with a $k_d$ less than $10^{-8}$. It is also more preferred that the aptamers bind the target molecule with a $k_d$ less than $10^{-10}$. It is also preferred that the aptamers bind the target molecule with a $k_d$ less than $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10 fold lower than the $k_d$ with a background binding molecule. It is more preferred that the aptamer have a $k_d$ with the target molecule at least 100 fold lower than the $k_d$ with a background binding molecule. It is more preferred that the aptamer have a $k_d$ with the target molecule at least 1000 fold lower than the $k_d$ with a background binding molecule. It is preferred that the aptamer have a $k_d$ with the target molecule at least 10000 fold lower than the $k_d$ with a background binding molecule. It is preferred when doing the comparison for a polypeptide for example, that the background molecule be a different polypeptide. For example, when determining the specificity of NF-κB or IκB aptamers, the background protein could be serum albumin. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$. It is more preferred that the triplex forming molecules bind with a $k_d$ less than $10^{-8}$. It is also more preferred that the triplex forming molecules bind the target molecule with a $k_d$ less than $10^{-10}$. It is also preferred that the triplex forming molecules bind the target molecule with a $k_d$ less than $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci.* USA 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162

5. Peptides a) Protein Variants

As discussed herein there are numerous variants of the NF-κB protein and IκB protein that are known and herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than from about 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| Alanine | AlaA |
| Allosoleucine | AIle |
| Arginine | ArgR |
| Asparagines | AsnN |
| aspartic acid | AspD |
| Cysteine | CysC |
| glutamic acid | GluE |
| Glutamine | GlnK |
| Glycine | GlyG |
| Histidine | HisH |
| Isolelucine | IleI |
| Leucine | LeuL |
| Lysine | LysK |
| Phenylalanine | PheF |
| Proline | ProP |
| pyroglutamic acidp | Glu |
| Serine | SerS |
| Threonine | ThrT |
| Tyrosine | TyrY |
| Tryptophan | TrpW |
| Valine | ValV |

TABLE 2

Amino Acid Substitutions

| Original Residue | Exemplary Conservative Substitutions, others are known in the art. |
|---|---|
| Ala | ser |
| Arg | lys, gln |
| Asn | gln; his |
| Asp | glu |
| Cys | ser |
| Gln | asn, lys |
| Glu | asp |
| Gly | ala |
| His | asn; gln |
| Ile | leu; val |
| Leu | ile; val |
| Lys | arg; gln; |
| Met | Leu; ile |
| Phe | met; leu; tyr |
| Ser | thr |
| Thr | ser |
| Trp | tyr |
| Tyr | trp; phe |
| Va | lile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [19831]), acetylation of the N-terminal amine and, in some instances, amidation of the C-terminal carboxyl.

6. Antibodies a) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with NF-κB or IκB such that NF-κB or IκB are inhibited from causing the cellular proliferative events disclosed herein. The antibodies can be tested for their desired activity using the in vitro assays described herein, or by analogous methods, after which their in vivo therapeutic and/or prophylactic activities are tested according to known clinical testing methods. Also disclosed are functional equivalents of antibodies.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such, antibodies, as long as they exhibit the desired antagonistic activity (See, U.S. Pat. No. 4,816,567 and Morrison et al., *Proc. Natl. Acad. Sci. USA*, 81:6851-6855 (1984)).

The disclosed monoclonal antibodies can be made using any procedure which produces mono clonal antibodies. For example, monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

b) Human Antibodies

The human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991).

The human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germline antibody gene array into such germ-line mutant mice results in the production of human antibodies upon antigen challenge.

c) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

d) Administration of Antibodies

Administration of the antibodies can be done as disclosed herein: Nucleic acid approaches for antibody delivery also exist. The broadly neutralizing anti NF-κB or IκB antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

7. Delivery of the Compositions to Cells a) Nucleic Acid Delivery

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

In the methods described herein, which include the administration and uptake of exogenous DNA into the cells of a subject (i.e., gene transduction or transfection), the nucleic acids can be in the form of naked DNA or RNA, or the nucleic acids can be in a vector for delivering the nucleic acids to the cells, whereby the encoding DNA or DNA or fragment is under the transcriptional regulation of a promoter, as would be well understood by one of ordinary skill in the art as well as enhancers. The vector can be a commercially available preparation, such as an adenovirus vector (Quantum Biotechnologies, Inc. (Laval, Quebec, Canada).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., Mol. Cell. Biol. 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood*

84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). The disclosed compositions and methods can be used in conjunction with any of these or other commonly used gene transfer methods.

As one example, if the antibody-encoding nucleic acid or some other nucleic acid encoding an inhibitor of the NF-κB or IκB proteins or encoding a particular variant of the NF-κB or IκB genes to be used in the disclosed methods, is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed compositions or vectors for example, lipids such as liposomes, such as cationic liposomes (e.g., DOTMA, s DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Feigner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

c) In Vivo/Ex Vivo

As described above, the compositions can be administered in a pharmaceutically acceptable carrier and can be delivered to the subjects cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

8. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

9. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter may be effective when a large number of animals is to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

c) Combinatorial Chemistry

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions interact with NF-κB or IκB such that the compositions decrease the cellular proliferative activity of NF-κB and IκB or portions thereof, where the compositions were identified using NF-κB or IκB as targets in a screening or selection protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, NF-κB or IκB are used as targets, or when the disclosed compositions like BAY-11-7082 or BAY-11-7085 are used in competitive inhibition assays are also disclosed. Thus, the products produced using the combinatorial or screening approaches that involve the disclosed compositions are also considered herein disclosed.

Combinatorial chemistry includes but is not limited to all methods for isolating small molecules or macromolecules that are capable of binding either a small molecule or another macromolecule, typically in an iterative process. Proteins, oligonuclecotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material-related to phage display and methods relate to combinatorial chemistry).

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen et al. (Cohen B. A.,et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example a portion of NF-κB or IκB is attached to a DNA binding domain of a transcriptional activation protein, such as Gal 4. By performing the two-hybrid technique on this type of system, molecules that bind desired fragments of NF-κB or IκB can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in iterative processes.

d) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions are also disclosed. Thus, the products produced using the molecular modeling approaches that involve the disclosed compositions are also considered herein disclosed.

10. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include molecules, including for example, BAY 11-7082 or BAY 11-7085 for use in in vitro cell assays as standards for anti-proliferative activity.

11. Compositions with Similar Functions

It is understood that the compositions, such as BAY 11-7082 and BAY 11-7085, disclosed herein have certain functions, such as antimetastatic activities or anti-proliferative activities. Disclosed herein are certain structural requirements for performing the disclosed functions, and it is understood that there are a variety of structures which can perform the same function which are related to the disclosed structures, and that these structures will ultimately achieve the same result, for example, inhibition of anti-proliferative activities.

E. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System IPlus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins or polypeptides is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant Ga. (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J.Biol.Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Processes for Making the Compositions

Disclosed are processes for making the compositions as well as making the intermediates leading to the compositions. There are a variety of methods that can be used for making these compositions, such as synthetic chemical methods and standard molecular biology methods. It is understood that the methods of making these and the other disclosed compositions are specifically disclosed.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

F. EXAMPLES

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 Materials & Methods a) Materials

The NF-κB inhibitors, BAY 11-7082 (Biomol), BAY 11-7085, (Biomol) and N-benzoyloxycarbonyl (Z)-Leu-Leu-leucinal (MG-132) (Sigma) were solubilized in DMSO. The antagonistic and chimeric TNFα monoclonal antibody (cA2) was purchased from the clinical pharmacy at the University of Utah and reconstituted in sterile water. Polyclonal antibodies to $FLIP_{S/L}$, c-IAP-1, c-IAP-2, TRAF-1, and TRAF-2 were obtained from Santa Cruz Biotechnology. Antibodies to cleaved poly(ADP-ribose) polymerase (PARP) were obtained from New England Biolabs. The monoclonal antibody recognizing the p65 NF-κB subunit was obtained from Santa Cruz. Alkaline phosphatase-conjugated goat-anti-rabbit antibody was obtained from Jackson Laboratories.

b) Cell Culture, Proliferation, and Toxicity

DLD-1, HCT-116, and HT-29 colon cancer cell lines were obtained from the ATCC collection and were cultured in Dulbecco's Modification of Eagle's Medium supplemented with 10% fetal bovine serum, glutamine, penicillin, and streptomycin. 293 cells stably transfected with COX-2 (293-COX-2) under the control of a ponasterone sensitive promoter were cultured in Dulbecco's Modification of Eagle's Medium supplemented with 10% fetal bovine serum, 400 μg/ml of zeocin, 400 μg/ml of G418, glutamine, penicillin, and streptomycin. For induction of COX-2 protein expression, 293-COX-2 cells were cultured for 48 hours in media supplemented with 1 μg/ml of ponasterone. All cells were cultured at 37° C. in a humidified incubator with a 5% $CO_2$ atmosphere.

For the cell proliferation assay, cells were dispersed and plated at 40,000 cells/well in 96-well dishes. At various days in culture, the cells were gently washed twice with 100 μl/well of ice-cold blocking buffer (1% radioimmunoassay grade BSA in PBS) and twice with 100 μl/well of ice-cold PBS. The cells were fixed for 10 min in 100% ice-cold methanol (100 μl/well), then allowed to air-dry. The cells were stained with 100μl/well of 0.1% crystal violet in $H_2O$ for 10 minutes, then washed gently four times with dd $H_2O$ and four times with PBS. The plates were then air-dried completely. The stained cells were then solubilized in 1% sodium deoxycholate, and the plates read at 590 nm in a spectrophotometer. The absorption at 590 nm is proportional to the number of attached cells.

For the cell toxicity assay, the CytoTox 96® kit from Promega was used according to the manufacturer's instructions. Briefly, DID-1, HCT-116, and HT-29 cells were incubated with 1, 2.5, 5, 7.5 and 10 μM BAY 11-7082 or BAY 11-7085 in 96-well plates for 24 hours then lysed by adding 15 μl of lysis 10×Solution (9% (v/v) Triton ® X-100 in water) per 100 μl of culture medium, followed by incubation at 37° C. for 45-60 minutes. Sample supernatants, (50 μl) were transferred to a fresh 96 well enzymatic assay plate and incubated with reconstituted Substrate Mix (50 μl per sample) for 30 minutes at room temperature in the dark. The enzymatic assay was then stopped by adding 50 μl/well of Stop Solution. The plate was read at 490 nm and the absorbance values plotted as a ratio to the controls (DMSO alone).

c) Electrophoretic Mobility Shift Assay

The adherent cell monolayers were washed once with cold PBS after which 200 μl of cold Buffer A (20 mM HEPES pH7.8, 1 mM EDTA, 1 mM EGTA, 10% glycerol, 0.2% NP-40, 0.2 mM $Na_3VO_4$, 1 mM DTT, 0.5 mM PMSF,and, 1 μg/ml each of aprotinin and leupeptin) was added to the cells. The cells were scraped into microfuge tubes, kept on ice, and sonicated. The lysates were centrifuged at 500 g for 5 min at 4° C. and the cytoplasmic fraction (supernatant) was removed. 25-50 μl of Buffer B (20 mM HEPES pH 7.8, 1 mM EDTA, 1 mM EGTA, 0.42M NaCl, 1.5 mM $MgCl_2$, 25% glycerol, 0.2 mM $Na_3VO_4$, 1 mM DTT, 0.5 mM PMSF, and, 10 μg/ml each of aprotinin and leupeptin) was added to the nuclear fraction (pellet). The suspension was vortexed, kept on ice for 30 minutes, and centrifuged at 13,000 g for 10 minutes. The supernatants (nuclear fraction) were normalized for total protein concentration using the BCA assay (Pierce).

5 pmol of a DNA oligonucleotide containing the NF-κB consensus binding site (5'-AGTTGAGGGGACTTTC-CCAGGC-3') (SEQ ID NO:1), 5 μl 5× forward reaction buffer, 10 units T4 polynucleotide kinase, 2.5 μl [$^{32}$P]ATP (10μCi/μl, 300 Ci/mmol), and water (to 25 μl total volume) were incubated for 10 minutes at 37° C. The reaction was stopped by heating the mixture for 10 min at 65° C. and the labeled oligonucleotide was separated from unincorporated [$^{32}$P]ATP by centrifuging the mixtures at 12,000-16,000 g for 30 seconds in G-25 Sepharose columns. The labeled nucleic acid was recovered in the collection tube in approximately 25 μl of TE buffer.

For the binding assays, equal amounts of nuclear extracts (approx 2-5 μg of protein) were incubated on ice for 15 minutes with 4 μl 5× gel shift binding buffer (50 mM Tris HCl pH 7.5, 250 mM KCl, 5 mM DTT, 1 mg/ml bovine serum albumin, 25% glycerol, H2O (volume adjusted to 5 ml.)), 1.5 μg poly (dI-dC), 1 μl $^{32}$P-labeled probe, and enough $H_2O$ to bring the total reaction volume to 20 μl. 2 μl 10× loading buffer (20% Glycerol, 0.1M $Na_2$EDTA pH 8, 0.25% bromphenol blue, 0.25% xylene cyanol) was added to each sample and then loaded onto a native 8% polyacrylamide gel. The gel was run in 0.5×TBE buffer for about 2 hours, dried, and subjected to autoradiography. The bands on the blots were quantified using the NIH Image program.

Activation of NF-κB was also determined using the Trans-AM™ assay (Active Motif, Carlsbad, Calif.) per the manufacturer's instructions. (Renard et al., 2001) Briefly, cell monolayers on 60 mm dishes were washed with ice-cold PBS and removed by incubating in trypsin-PBS or scraping. The cells were centrifuged for 10 minutes at 1,000 rpm at 4° C. and resuspended for 10 minutes in 100 μl of 4° C. lysis buffer (20 mM HEPES (pH 7.5), 350 mM NaCl, 20% glycerol, 1% Igepal-CA630, 1 mM $MgCl_2$, 0.5 mM EDTA, 0.1 mM EGTA, 1 μl of 1 M dithiothreitol and 10 μl of protease inhibitor cocktail (proprietary) per ml of lysis buffer). The lysates were centrifuged for 20 minutes at 14,000 g at 4° C. Lysates containing 5 μg of total protein were added to 20 μl of lysis buffer per well in 96-well dishes containing immobilized oligonucleotides corresponding to the NF-κB consensus DNA binding site (5'-GGGACTTTCC-3') (SEQ ID NO:2). The plate was covered with an adhesive film and incubated for 1 hour at room temperature on a rocker. The wells were then washed three times with 200 μl per well of washing buffer (100 mM phosphate buffer (pH 7.5), 500 mM NaCl, 1% Tween). 100 μl of p65subunit monoclonal antibody (the p65 antibody supplied with the kit only recognizes p65-containing NF-κB heterodimers that are bound to DNA containing the NF-κB consensus binding sequence) was diluted 1:1,000 in 1× antibody binding buffer (4 mM HEPES (pH 7.5), 120 mM KCl, 8% glycerol, 1% bovine serum albumin) and added to each well and incubated for 1 hour at room temperature. The wells were washed with 100 µl of washing buffer three times. 100 µl of horseradish peroxidase-conjugated secondary antibody diluted 1:1,000 in 1× antibody binding buffer was added to each well and incubated for 1 hour at room temperature without agitation. The wells were washed four times with 200 µl per well of 1× washing buffer. 100 µl of developing solution (tetramethylbenzidine in 1% DMSO) was added to each well and incubated for 10 minutes at room temperature. 100 µl of stop solution (0.5 M $H_2SO_4$) was added to each well after which the absorbance was determined on a plate spectrophotometer at 450 nm. Specificity of binding was determined using 200-fold excess wildtype NF-κB oligonucleotides added at the time the cell lysates were added to the wells.

d) Apoptosis Assay

Single cell suspensions were plated at 100,000 cells per well in 24-well plates in media containing DMSO, BAY 11-7082, BAY 11-7085, or MG-132 for 8-24 hours in an incubator. Alternatively, DMSO, BAY 11-7082, BAY 11-7085, or MG-132 were added to cells that were confluent and adherent for several days. The nonadherent cells were aspirated off with the media and spun for 3 minutes at 2,000 rpm in 15 ml polypropylene tubes. The adherent cells were washed twice with PBS, dispersed in trypsin, and spun down for 3 minutes at 2,000 rpm in 15 ml polypropylene tubes. The nonadherent and adherent cells were resuspended in 1× binding buffer (10 mM HEPES/NaOH, pH 7.4, 140 mM NaCl, and 2.5 mM $CaCl_2$) to a final concentration of $10^6$ cells/ml. 100 µl of the cell solution were transferred to a 5 ml culture tube and incubated with 5 µl of annexin V-FITC-conjugated monoclonal antibody (Pharmingen) and 10 µl of propidium iodide (from a 50 µg/ml stock solution made in PBS) in the dark at 25° C. for 15 minutes. 400 µl of binding buffer was added to each tube and the cells were analyzed by flow cytometry immediately. The percent of apoptosis was determined as the percent of annexin V-positive, propidium iodide-negative cells of the total cells counted.

DLD-1 and HT-29 cells that were approximately 60-70% confluent were transduced with Ad-IκB super-repressor by adding 1-50 µl of purified virus to the cells. After 3 days, the expression of the IκB super-repressor was ascertained by immunoblot. In a parallel experiment, the transduced cells were resuspended and allowed to readhere in BAY 11-7085 for 8 h. The percentage of surviving (nonapoptotic) cells was determined using crystal violet staining.

e) Immunoblotting

The cells were washed twice in ice cold PBS and then lysed in 4° C. lysis buffer (50 mM HEPES, 150 mM NaCl, 1.5 mM $MgCl_2$, 1 mM EGTA, 100 mM NaF, 10 mM $Na_2PO_4$, 1 mM $Na_3VO_4$, 10% glycerol, 1% Triton X-100, and 1 µg/ml each of aprotinin, leupeptin, chymostatin, pepstatin) and clarified at 12,000 rpm at 4° C. for 15 minutes. The lysates were normalized for total protein concentration. Aliquots of the lysates were then mixed 1:1 in sample buffer (125 mM Tris-HCl (pH 6.8), 20% glycerol. 4% sodium dodecyl sulfate, 2% beta-mercaptoethanol, 10 µg/ml bromophenol blue) and boiled for 3 minutes. The samples were loaded onto SDS-PAGE gels (7.5 or 10% acrylamide). The proteins were transferred to nitrocellulose from the gels, then incubated in blocking buffer (1% bovine serum albumin (Bio-Rad), 100 mM Tris-Cl (pH7.4), 0.9% NaCl, 0.1% Nonidet) overnight at 4° C.

For immunodetection, the blocked blots were probed with primary antibody for 2 hours at 4° C. on a rocker. The blots were washed twice for 10 minutes each in blocking buffer, then incubated with a 1:2000 dilution of a rabbit-anti-mouse secondary antibody (for monoclonal primary antibodies; for polyclonal antibodies, this step was skipped). After two washes in blocking buffer (150 mM NaCl, 20 mM Tris pH 7.4, 0.5% Tween 20, 5% bovine serum albumin, and 0.2 gm/500 ml final concentration of sodium azide), the blots were finally incubated with a 1:2000 dilution of alkaline phosphatase-conjugated rabbit-anti-mouse antibodies (Jackson) in blocking buffer. Alkaline phosphatase was detected by a colorimetric reaction using a BCIP (5-Bromo-4-Chloro-3-Indolyl phosphate)/NBT (Nitroblue tetrazolium) kit (Zymed).

f) Athymic Mouse Colon Cancer Xenograft Studies

HT-29 and HCT-116 cells were harvested in 0.25% trypsin-PBS-EDTA, washed once in media and PBS, and resuspended in PBS at 1 million cells per 200 µL. One million cells were injected either subcutaneously in the backs or intraperitoneally in 5 week old female nu/nu athymic mice (Charles River Labs). For the mice with subcutaneous tumors, the tumors were allowed to establish themselves for 10 days after which they were randomized to BAY 11-7085 or DMSO. For the mice with intraperitoneal tumors, the mice received DMSO or BAY 11-7085 (5 mg/kg) 24 hours before the cancer cells were injected intrapentoneally. All mice received BAY 11-7085 (5 mg/kg) or an equal volume of DMSO (~200 µL) twice weekly for 21-32 days. Subcutaneous tumor sizes were determined by measuring the length and width with calipers. These studies were approved by the U. of Utah Institutional Review Board and Institutional Animal Care and Use Committee and performed in the Animal Resource Center. Mice were euthanized when they experienced a greater than 10% loss in body weight or if they appeared ill. Post-mortem examinations included sectioning of kidney, lung, and liver tissues which were stained with hematoxylin and eosin followed by examination for tissue toxicity/damage by an experienced mouse pathologist (E.J.E.) who was blinded to therapy.

2. Example 2. Results a) NF-κB Inhibitors Diminish Colon Cancer Cell Proliferation Two compounds, BAY 11-7082 and BAY 11-7085, known to inhibit NF-κB and arthritis in rodent models (Pierce et al., 1997) were tested on colon cancer cell lines. BAY 11-7082 and BAY 11-7085 are soluble compounds that inhibit IκB phosphorylation and TNFα-induced NF-κB activation. (Pierce et al., 1997) They were also found to activate JNK/SAPK and p38, members of the MAP kinase family of signal transduction proteins. (Pierce et al., 1997) Incubation of the colon cancer cell lines, DLD-1, HCT-116, HT-29, with 10 µM of BAY 11-7085, but not BAY 11-7082 greatly inhibited cell proliferation (FIGS. 1A & B).

In order to determine whether the differences in the inhibitory effects of BAY 11-7082 and BAY 11-7085 on colon cancer cell proliferation were due to differences in the activities of the two compounds, NF-κB electrophoretic mobility shift assays (EMSA) were performed. Following 3 and 6 hour incubations of HT-29 cells with the two compounds at 10 µM concentrations, a more profound inhibition of NF-κB activity occurred with BAY 11-7085 than BAY 11-7082 (FIG. 1C). Consistent with previous reports in a variety of cancer cells, HT-29 colon cancer cells demonstrated constitutive activation of NF-κB. DLD-1 and HCT-116 cells demonstrated constitutive activation of NF-κB by EMSA as well (data not shown).

When HT-29 colon cancer cells were treated with the NF-κB inhibitors, BAY 11-7085 or MG-132 for 24 h, the percentage of apoptotic cells (annexin V-positive and propidium iodide-negative) was relatively greater for MG-132 than BAY 11-7085, and was proportional to the number of floating cells. It was confirmed in HT-29 cells that were treated with increasing concentrations of BAY 11-7085 for 24 h. After separating the HT-29 cells that remained adherent and those that became nonadherent after BAY 11-7085 treatment, the percentage of apoptotic cells was determined for each group. Whereas the majority of nonadherent cells were apoptotic, only a minority of the adherent cells was apoptotic. The percentage of non-adherent apoptotic cells decreased after treatment with 50 and 100 µM BAY 11-7085 compared with lower concentrations of BAY 11-7085, because many of the cells were positive for both annexin V and propidium iodide indicating that they had completed apoptosis and were now necrotic. Shown another way, HT-29 cells were treated with 20 µM MG-132 for 8 h, after which the adherent and nonadherent cells were collected separately, and then lysed and immunoblotted for cleaved PARP, a product of caspase cleavage. Whereas there was only a small increase in cleaved PARP in the cells that remained adherent, there was a large increase in cleaved PARP in the nonadherent cells. It has been shown that the loss of colon cancer cell adhesion was associated with the induction of apoptosis by IFN and TNFα. The inhibition of colon cancer cell adhesion appears to be related to the apoptotic effects of the NF-κB inhibitors.

In order to determine whether BAY 11-7082 or BAY 11-7085 caused significant direct cell toxicity, an LDH-based cell toxicity assay was performed on DLD-1, HCT-116, and HT-29 cell lines. One to ten µM 11-7082 or 11-7085 for 24 hours resulted in a maximum of 20% cell toxicity. Thus, direct cell toxicity due to BAY 11-7082 or BAY 11-7085 could not alone explain the decreased colon cancer cell proliferation.

b) NF-κB Inhibitors Inhibit Colon Cancer Cell Tumorigenicity

Anchorage-independent cell growth is a hallmark of cancer cells and is a good correlate to tumorigencity in vivo. Therefore, the effects of BAY 11-7082 and BAY 11-7085 were examined on colon cancer cell growth using the soft agar colony formation assay. At 10 µM concentrations of BAY 11-7082 or BAY 11-7085 for 6 days, anchorage-independent proliferation of the DLD-1 and HT-29, but not HCT-116, colon cancer cell lines was significantly inhibited (FIG. 2A).

A recent study showed that inhibition of NF-κB in colon cancer cell xenografts in athymic mice by direct injection of adenovirus containing the IκB super-repressor mutant into the tumors alone failed to reduce the tumor size. (Wang et al., 1999) However, BAY 11-7082 or BAY 11-7085 alone inhibit colon cancer xenograft growth in athymic mice. HC-116, and HT-29 cell lines were used to generate subcutaneous tumors in athymic female mice. The mice were subsequently randomized to be treated with vehicle (DMSO) alone or BAY 11-7085 1 mg/kg twice weekly for 28 days.

Figure 2C:
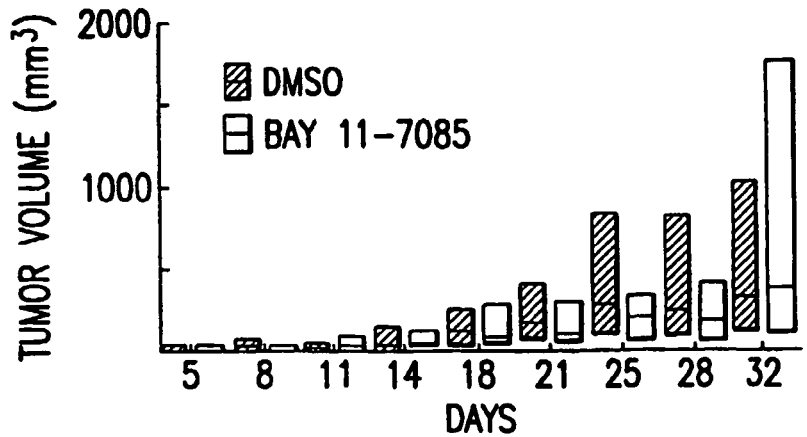
Figure 3A:
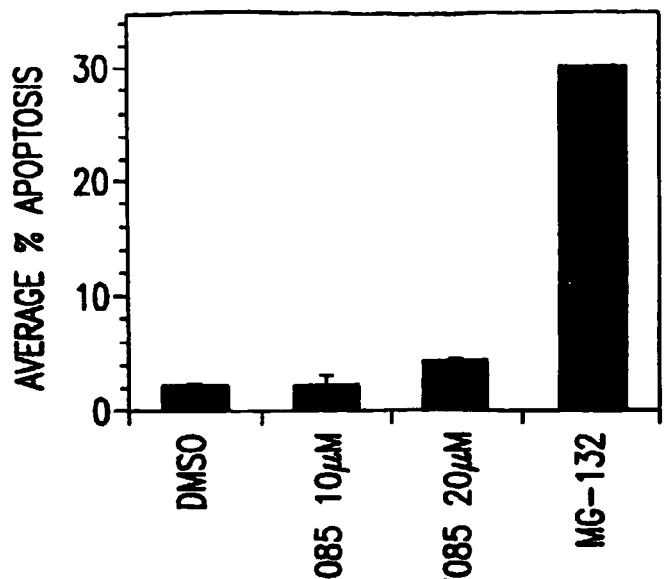
Figure 3B:
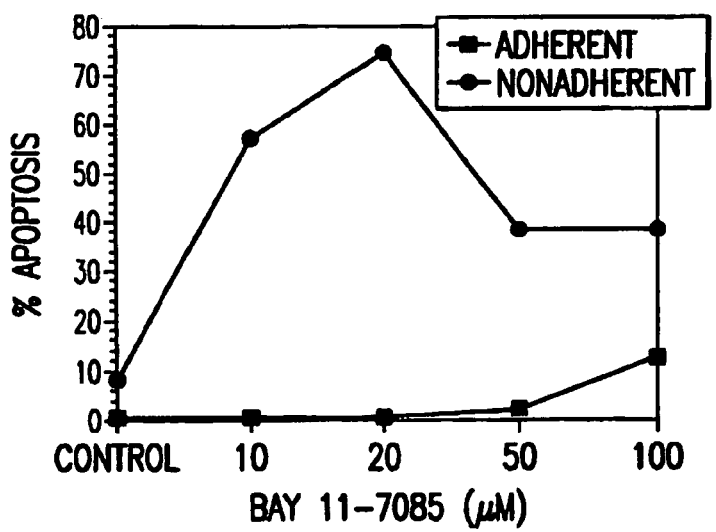
Figure 3D:
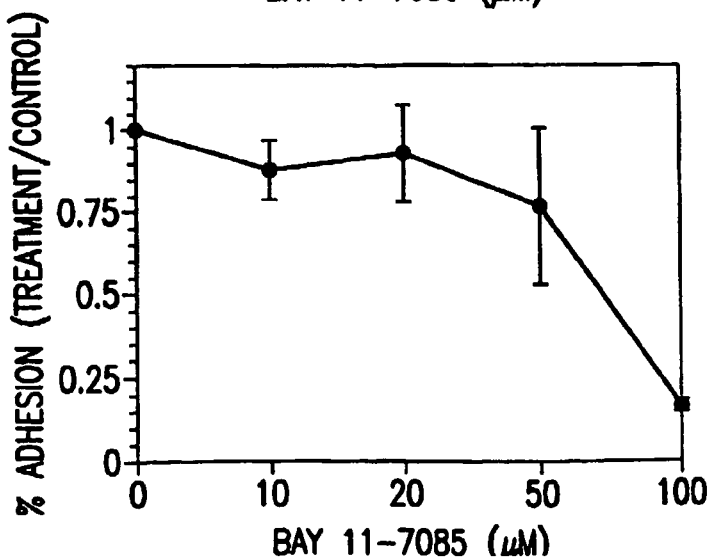
Figure 3C:
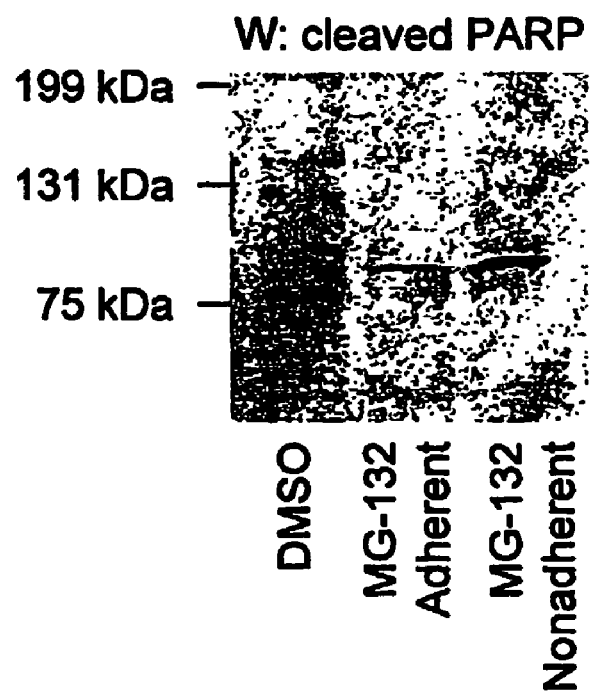

While HT-29 cells readily formed tumors in the athymic mice, HCT-116 cells formed only very small tumors in most cases. There was a statistically significant overall reduction in the tumor volumes in the HT-29 xenografts in the BAY 11-7085 treatment group compared with the control group (FIG. 2B). There was no statistically significant overall difference in the tumor volumes in the HCT-116 xenografts in the treatment or control groups (FIG. 2C).

c) NF-κB Inhibitor-Induced Apoptosis is Associated with a Loss and Inhibition of Cell Adhesion Treatment of HT-29 cells with BAY 11-7082 or BAY 11-7085 at doses up to 20 µM for 24 hours caused an increase in the level of apoptosis as measured by the annexin V-FITC assay (FIG. 3A), which is sensitive for cells in the early stages of apoptosis. However, 20 µM MG-132, another NF-κB inhibitor, caused a greater increase in apoptosis (FIG. 3A). Disclosed herein, the level of apoptosis correlated with the degree of loss of cell adhesion manifested by floating cells. HT-29 cells were treated with increasing concentrations of BAY 11-7085 for 8 hours, after which the percentage of apoptotic cells was determined separately for the cells that remained adherent and those that became non-adherent. While the non-adherent cells were predominantly apoptotic, only a minority of the adherent cells was apoptotic (FIG. 3B). Note that the percentage of apoptosis in the non-adherent cell fraction decreased at 50 and 100 µM concentrations of BAY 11-7085. This was due to the fact that after 8 hours of treatment, many of the cells at higher doses of BAY 11-7085 were annexin V-positive and failed to exclude propidium iodide meaning that they had completed apoptosis and were now necrotic. Similar results were obtained using another colon cancer cell line, HCT-116, and MG-132. Following treatment of HCT-116 cells with 20 µM MG-132 for 24 hours there was a readily apparent population of cells that had lost adhesion. While there was only a small increase in cleaved PARP, a product of caspase cleavage and activation, in the cells that remained adherent, there was a large increase in cleaved PARP in the non-adherent cells (FIG. 3C).

Pretreatment of adherent HT-29 cells for three days with various concentrations of BAY 11-7085 followed by a one-hour cell adhesion assay demonstrated a significant and rapid inhibition of cell adhesion at high concentrations of BAY 11-7085 (FIG. 3D), suggesting that NF-κB promoted cell adhesion. Even though BAY 11-7085 induced a loss of cell adhesion, it was important to show whether HT-29 cells were actually susceptible to anoikis. When HT-29 cells were cultured in suspension for 24 hours on dishes coated with poly-HEMA, a substrate that completely inhibited HT-29 cell adhesion, only a minority (17%) of the floating cells were apoptotic by the annexin V assay. The fact that only a small fraction of suspended HT-29 cells were apoptotic, suggested that anoikis was not the principal mechanism responsible for the apoptotic activity of the NF-κB inhibitors.

d) Loss of Colon Cancer Adhesion Activates NF-κB

Various concentrations of BAY 11-7085 were added to HT-29 cells that were transiently suspended in trypsin-PBS for approximately 15 minutes before replating. The transiently suspended cells were quickly allowed to readhere in order to prevent anoikis. Alternatively, BAY 11-7085 was added to adherent HT-29 cell monolayers. BAY-11-7085 at all concentrations tested caused a significant increase in apoptosis of the transiently suspended HT-29 cells (FIG. 4A). On the other hand, even the highest doses of BAY 11-7085 caused only a relatively small degree of apoptosis of adherent compared with transiently suspended HT-29 cells (FIG. 5). Similar results were obtained with BAY 11-7082 at the same doses.

Since a transient loss of cell adhesion greatly enhanced the apoptotic effect of BAY 11-7085, we hypothesized that activation of NF-κB may be effected by a loss of cell adhesion. To test this, DLD-1, HCT-116, and HT-29 cells were transiently suspended in trypsin-PBS and then quickly allowed to readhere. Immunofluorescent studies on the localization of the p65 NF-κB subunit revealed nuclear p65 in cells one hour after being transiently in suspension (FIG. 4B). This was followed by a decrease in nuclear p65 localization from 3-24 hours after replating. In fact, by 24 hours, little nuclear p65 staining was seen although much cytoplasmic p65 staining was present. Similar results were obtained with DLD-1 (FIG. 4C) and HCT-116 (FIG. 4D) colon cancer cell lines. These results demonstrated that transient suspension of colon cancer cells resulted in activation of NF-κB.

An NF-κB binding assay was used to demonstrate the activation of NF-κB by transient suspension. Adherent monolayers of DLD-1, HCT-116, and HT-29 cells were treated with increasing concentrations of BAY 11-7085 for 8 hours were scraped off plates and subjected to an NF-κB activation assay. The scraped cells were lysed and added to 96-well plates containing immobilized oligonucleotides corresponding to the NF-κB consensus binding sequence (Trans-AM® assay). NF-κB binding to the immobilized oligonucleotides was detected using a p65 monoclonal primary antibody and a horseradish peroxidase-conjugated anti-mouse secondary antibody. The assay showed that there was relatively little activation of NF-κB compared to the positive control (HeLa cells treated with TNFα) (FIG. 5A). However, when the transiently suspended cells were allowed to readhere, a large induction of NF-κB activation occurred (FIG. 5A). Thus it was re-adhesion rather than just transient suspension that was the stimulus causing the large increase in NF-κB activation.

The same NF-κB binding assay was used to determine whether NF-κB inhibitors could diminish the activation of NF-κB by re-adhesion. HT-29 cells transiently suspended with trypsin were mixed with increasing concentrations of BAY 11-7085 then placed on culture dishes for 8 hours. Alternatively, adherent HT-29 cells were treated with increasing concentrations of BAY 11-7085 for 8 hours. The cells were scraped, and all the cells were collected and lysed. The NF-κB binding assay confirmed the strong activation of NF-κB caused by the readhesion of transiently suspended HT-29 cells and demonstrated a dose-related inhibition of this NF-κB activation by BAY 11-7085 (FIG. 5B, transiently suspended cells). On the other hand, there was a steady and low level of constitutive NF-κB activation in the adherent HT-29 cells that was relatively unaffected by treatment with increasing concentrations of BAY 11-7085 (FIG. 5B, adherent cells).

Since trypsin can activate protease-activated receptor-2 in colon cancer cell lines, which then results in increased cell proliferation, (Darmoul et al., 2001) NF-κB activation was determined in adherent and confluent DLD-1, HCT-116, Caco-2 and HT-29 cells that were removed from plastic dishes by trypsin or scraping. Scraping of the cells did not result in NF-κB activation (FIG. 5C). In addition, cells that were transiently suspended in trypsin-PBS but not allowed to readhere, did not show significantly more activation of NF-κB by the TransAM assay (FIG. 5C). To determine whether the transient activation of NF-κB caused by cell readhesion would render all of the colon cancer cells tested more susceptible to BAY 11-7085-induced apoptosis, DLD-1, HCT-116, Caco-2 and HT-29 colon cancer cell lines were transiently suspended, treated with BAY 11-7085 and allowed to read-here. While DLD-1 and HT-29 cells showed the same propensity for BAY 11-7085-induced apoptosis, Caco-2 cells showed a moderate increase, while HCT-116 cells did not (FIG. 5C).

The colon cancer cell lines used were chosen for differences in their origins. While DLD-1 and HT-29 cells carry mutated APC alleles, HCT-116 cells do not, (Groden et al., 1995) however, HCT-116 cells carry activating mutations in the β-catenin gene (CTNNB1), (Ilyas et al., 1997) whose gene product is normally regulated by the APC gene product. (Munemitsu et al., 1995; Rubinfeld et al., 1995) In addition, HCT-116 cells do not express COX-2 while DLD-1 and HT-29 cells do. (Hsi et al., 2000; Shao et al., 2000; Tsuji et al., 1996) COX-2 is commonly overexpressed in colorectal tumors and plays roles in survival and metastasis in colorectal cancers.

COX-2 overexpression plays a role in the susceptibility of the colon cancer cells to BAY 11-7085-induced apoptosis. 293 cells transfected with a ponasterone-inducible COX-2 construct (293-COX-2) were treated with BAY 11-7085. Treatment of 293-COX-2 cells with 1 μg/ml of ponasterone for 48 hours led to a large induction of COX-2 protein, while the uninduced cells showed no measurable COX-2 protein expression by western blot (FIG. 5E) Uninduced 293-COX-2 cells showed no increase in apoptosis following treatment with BAY 11-7085 (FIG. 5F). However, ponasterone-induced 293-COX-2 cells demonstrated a marked increase in BAY 11-7085-induced apoptosis (FIG. 5E). This data indicated that differences in COX-2 expression can influence the ability of BAY 11-7085 to cause apoptosis.

Two other soluble NF-κB inhibitors, MG-132 and PDTC, were used to test their activity in the induction of apoptosis of colon cancer cells during readhesion. Compared with BAY 11-7085, MG-132 more potently induced apoptosis of HT-29 colon cancer cells during readhesion. PDTC caused apoptosis of HT-29 cells during readhesion as well.

The specific involvement of NF-κB in the apoptotic mechanism of BAY 11-7085 was examined specifically. To accomplish this, DLD-1 and HT-29 cells were transduced with an adenovirus containing the IκB super-repressor construct to specifically inhibit NF-κB. The IκB super-repressor was created previously by mutating two key serine residues within the IκB gene resulting in an encoded IκB protein that is incapable of being targeted for ubiquitination and, hence, degradation by the proteasome. The transduced DLD-1 and HT-29 cells were then transiently suspended and allowed to readhere at concentrations of BAY 11-7085 below the in vitro apoptotic threshold (>20 μM) for these cell lines. Expression of the IκB super-repressor in DLD-1 and HT-29 cells significantly lowered the apoptotic threshold of BAY 11-7085 compared with the controls. The effect of the IκB super-repressor was much greater for DLD-1 than HT-29 cells because the former expressed higher levels of IκB super-repressor protein than the latter cells. Furthermore, the IκB super-repressor protein was functional in both cell lines. Therefore, inhibition of NF-κB is important to the apoptotic effect of BAY 11-7085 during colon cancer cell readhesion.

e) NF-κB Inhibitor Prevents Intraabdominal Metastasis In Vivo

Since BAY 11-7085 induced apoptosis of readherent HT-29 cells, an in vivo model was used to test the ability of the drug to prevent metastasis by seeding of intraabdominal tissue with colon cancer cells. During colorectal cancer surgery, seeding of the peritoneal cavity by tumor cells with tumor cell implantation of the peritoneal surfaces can occur. Seeding results from the transient suspension of cancer cells, through a loss of adhesion either naturally ro because of surgical displacement, followed by readhesion to other tissues. The HT-29 and HCT-116 colon cancer cell lines were injected into the abdominal cavities of athymic mice that had been pretreated 24 hours earlier with either intraperitoneal vehicle alone (DMSO) or BAY 11-7085 (1 mg/kg). The mice were then treated twice weekly with vehicle or BAY 11-7085 for a total of 21 days. Mice sacrificed 7 days after the introduction of colon cancer cells intraabdominally showed no evidence of tumoral implantation of the parietal or visceral peritoneal surfaces.

Figure 6A:
Figure 6B:

After 21 days, there was clear evidence of metastases involving the parietal and visceral peritoneum of mice injected with HCT-116 cells regardless of whether they had received vehicle or BAY 11-7085 (FIGS. 6A and B). However, of the mice injected intraabdominally with HT-29 cells and treated with BAY 11-7085, only 2 of 6 mice demonstrated parietal peritoneal metastases and none of the 6 showed any evidence of hepatic metastases (Table 1).

TABLE 1

Peritoneal and liver metastases following intraperitoneal injections of HT-29 cells into athymic mice.

| Treatment | Peritoneal Metastases | Liver Metastases |
| --- | --- | --- |
| DMSO (n = 6) | 5/6 | 6/6 |
| BAY 11-7085 (n = 6) | 2/6 | 0/6 |

Figure 6C:
Figure 6D:
Figure 6E:
Figure 6F:
Figure 6G:
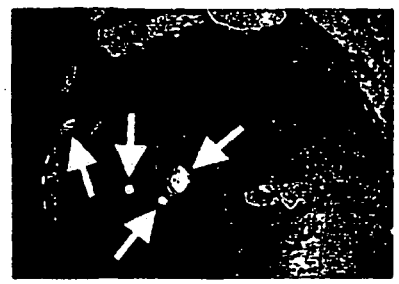
Figure 6H:
Figure 6I:
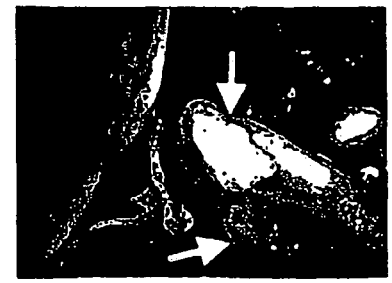

Of the mice that had been injected intraabdominally with HT-29 cells and treated with vehicle, 5 of 6 developed metastases of the parietal peritoneum and all 6 developed hepatic metastases (FIG. 6C and Table 1). Interestingly, the majority of the metastases involved ventral and dependent areas of parietal and visceral peritoneum, suggesting that the colon cancer cells took some time to implant.

f) NF-κB Inhibitors Decrease Expression of Anti-Apoptotic Proteins

Inhibition of NF-κB increased the susceptibility of cancer cells to TNFα-induced apoptosis in other studies. (Han et al., 2000; Wang et al., 1999) Furthermore, TNFα is expressed by a number of colon cancer cell lines including HT-29 cells. (Jung et al., 1995) In order to explore the possibility that BAY 11-7082 and BAY 11-7085 may be sensitizing colon cancer cells to TNFα-induced apoptosis, HT-29 cells were pretreated with a monoclonal antibody, cA2, which inhibits TNFα binding to TNFα receptors, (D'Haens et al., 1999) followed by treatment with BAY 11-7085. A previous study demonstrated TNFα-induced activation of NF-κB in HT-29 cells. (Yamamoto et al., 1999) In order to ascertain whether cA2 alone had any measurable effects on colon cancer cells, DLD-1, HCT-116, and HT-29 colon cancer cells were treated with various concentrations of cA2 in a cell proliferation assay. Interestingly, cA2, at 10 and 50 μg/ml, caused a significant inhibition of colon cancer cell proliferation after several days of treatment (FIG. 7A). However, pretreatment of transiently suspended HT-29 cells with 50 μg/ml of cA2 for 48 hours did not diminish BAY 11-7085-induced apoptosis of adherent (FIG. 7B). This indicated that endogenous TNFα was not necessary for BAY 11-7085-induced apoptosis.

NF-κB regulates the expression of a number of genes, including c-IAP-1, c-IAP-2, TRAF-1, and TRAF-2, that encode proteins that mediate cell survival. (Stehlik et al., 1998; Wang et al., 1998; Wu et al., 1998) No decrease in c-IAP-1 protein expression occurred when transiently suspended or adherent HT-29 cells were treated with 20 μM of BAY 11-7085 for 8 hours (FIG. 7C). HT-29 cells did not express detectable levels of c-IAP-2 by western blots. The same treatment of HT-29 cells did result in a decrease in the protein expression of both TRAF-1 and TRAF-2 proteins (FIG. 7C).

Recently, the anti-apoptotic protein, FLIP, which inhibits TNFα-mediated apoptosis, was found to be regulated by NF-κB and overexpressed in a variety of cancers. (Elnemr et al., 2001; Irmler et al., 1997; Kreuz et al., 2001; Ryu et al., 2001; Tepper and Seldin, 1999) Interestingly, FLIP expression is upregulated by cell adhesion in endothelial cells and plays a role in inhibiting anoikis. (Aoudjit and Vuori, 2001) Disclosed herein FLIP was expressed in the DLD-1 and HT-29, but not the HCT-116, cell lines. Twenty μM BAY 11-7085 caused only a slight diminution in the expression of the 54 kilodalton (long) isoform of FLIP in adherent, but not transiently suspended, HT-29 cells (FIG. 7C). Although decreased FLIP expression could be involved in BAY 11-7085-induced apoptosis of HT-29 cells, it would not explain BAY 11-7085-induced apoptosis in DLD-1 cells since they do not express FLIP (FIG. 7D).

Treatment of adherent colon cancer cells with BAY 11-7082, BAY 11-7085, or MG-132 inhibited colon cancer cell proliferation, tumorigenicity, and adhesion, and induced apoptosis. These effects were not uniform amongst the selected colon cancer cell lines used. While the cell proliferation of all three cell lines were readily inhibited by BAY 11-7085, reduced tumorigenicity and apoptosis induction by treatment with BAY 11-7082 and BAY 11-7085 was only achieved in the DLD-1 and HT-29 cell lines. Results obtained using ponasterone-inducible COX-2 transgene expression in 293 cells demonstrated a likely role for COX-2 protein expression or ovexpression in the apoptotic response to BAY 11-7085.

While cells that became non-adherent following treatment with NF-κB inhibitors were apoptotic, those cells that remained adherent were not. In addition, pretreatment of HT-29 cells with BAY 11-7085 caused a significant inhibition of cell adhesion at higher doses. The proapoptotic effect of BAY 11-7085 was greater when it was added to transiently suspended HT-29 and DLD-1 cells (i.e.-just before plating) versus adherent cells. These results indicated that transient suspension of colon cancer cells increased the susceptibility of the cells to apoptosis due to NF-κB inhibition.

When adherent DLD-1, HCT-116, and HT-29 cells were scraped off of plastic dishes and assayed for NF-κB activation, the level of NF-κB DNA binding was low relative to the positive control (HeLa cells stimulated with TNFα). When transiently suspended DLD-1, HCT-116, and HT-29 were allowed to readhere, there was a rapid and large activation (similar to the positive control) and increased nuclear localization of NF-κB. Thus, it was the readhesion of the transiently suspended colon cancer cells that activated NF-κB. This large activation of NF-κB induced by the readhesion of transiently suspended colon cancer cells was rapid and almost totally inhibited by treatment with as little as 10 μM BAY 11-7085. On the other hand, adherent colon cancer cells demonstrated a low but constitutive level of NF-κB activation, which could not be inhibited with doses of BAY 11-7085 up to 50 μM.

It appears that NF-κB inhibitors cause apoptosis of colon cancer cells in a two-step process. First, the NF-κB inhibitors inhibit cell adhesion of adherent colon cancer cells in vitro. The re-adhesion of these floating cells causes a large and transient activation of NF-κB. This renders the readherent cells exquisitely susceptible to NF-κB inhibitor-induced apoptosis. The fact that the vast majority of transiently suspended HT-29 and DLD-1 cells, which were allowed to readhere, became apoptotic following treatment with BAY 11-7082 or BAY 11-7085, indicated that NF-κB is an important survival factor for certain cancer cells, such as colon cancer cells, during the process of re-adhesion, particularly cancer cells that express COX-2 and/or mutant APC genes.

As metastatic cancers must transiently suspend to pass through the circulatory system and then readhere to be invasive, these results indicate that the compositions disclosed herein can be used for the prevention of metastasis The process of metastasis has been proposed to involve a number of sequential steps: invasion, dissociation, intavasation into the circulatory or lymphatic systems, dissemination, arrest in the microcirculation, extravasation, and invasion of distant tissues. (Engers and Gabbert, 2000) Each of these steps involves dynamic changes in cell adhesion including a complete absence of adhesion during dissemination. Although circulating cancer cells in humans can be abundantly found in venous blood samples of advanced cancer patients, (Mehes et al., 2001) Fortunately, the process of metastasis is surprisingly inefficient with as few as 0.05% of circulating tumor cells producing stable metastases. (Liotta et al., 1974; Nicolson, 1991; Weiss, 1985) Although many circulating tumor cells become arrested in the microcirculation, the majority of these cells remain viable and capable of extravasation in vivo. (Chambers et al., 1995) Thus, the rate limiting step in metastasis is the colonization of distant tissues by extravasated tumor cells (Chambers et al., 1995).

While the five-year survival rate for early stage colorectal cancers (TNM I-II) without metastases is greater than 80%, for late-staged cancers (TNM III-IV) with metastases it is less than 50%.(Boland, 1999) Most newly diagnosed colorectal cancers are TNM stage III-IV, which means that most colorectal cancer patients already have metastasis of the primary tumor by the time of presentation. In fact, micrometastasis to lymph nodes was detected by RT-PCR of carcinoembryonic antigen in 54% of patients deemed to be TNM stage II by current staging methods. (Liefers et al., 1998). In this study, the five-year survival of the patients with lymph node micrometases was 50% versus 91% for those without micrometases. This means that the stage II patients with micrometastases behaved clinically more like TMN stage III patients with regards to survival. Thus, a greater proportion of newly diagnosed colorectal cancers already have metastases than previously thought. Indeed, breast cancer cells in the blood of patients with advanced breast cancer were found as frequently as 1 per 1000 mononuclear cells. (Mehes et al., 2001) Although the majority of these cells were apoptotic, a minority were not, demonstrating that a significant number of cancer cells invade into the circulatory system and survive.

G. References

1. Alkalay, I., Yaron, A., Hatzubai, A., Orian, A., Ciechanover, A., and Ben-Neriah, Y. (1995). Stimulation-dependent I kappa B alpha phosphorylation marks the NF-κB inhibitor for degradation via the ubiquitin-proteasome pathway, Proc Natl Acad Sci USA 92, 10599-603.
2. Aoudjit, F., and Vuori, K. (2001). Matrix attachment regulates Fas-induced apoptosis in endothelial cells: a role for c-flip and implications for anoikis, J Cell Biol 152, 633-43.
3. Battu, S., Chable-Rabinovitch, H., Rigaud, M., and Beneytout, J. L. (1998). Cyclooxygenase-2 expression in human adenocarcinoma cell line HT29 cl.19A, Anticancer Res 18, 2397-403.
4. Beg, A. A., Ruben, S. M., Scheinman, R. I., Haskill, S., Rosen, C. A., and Baldwin, A. S., Jr. (1992). I kappa B interacts with the nuclear localization sequences of the subunits of NF-κB: a mechanism for cytoplasmic retention, Genes Dev 6, 1899-913.
5. Boland, C. R. (1999). Malignant Tumors of the Colon. In Textbook of Gastroenterology, T. Yamada, D. H. Alpers, L. Laine, C. Owyang, and D. W. Powell. eds. (Philadelphia. Lippincott Williams and Wilkins), pp. 2023-2082.
6. Cao, S., Troutt, A. B., and Rustum, Y. M. (1998). Interleukin 15 protects against toxicity and potentiates antitumor activity of 5-fluorouracil alone and in combination with leucovorin in rats bearing colorectal cancer, Cancer Res 58, 1695-9.
7. Chambers, A. F., MacDonald, I. C., Schmidt, E. E., Koop, S., Morris, V. L., Khokha. R., and Groom, A. C. (1995). Steps in tumor metastasis: new concepts from intravital videomicroscopy, Cancer Metastasis Rev 14, 279-301.
8. Chen, Z., Hagler, J., Palombella, V. J., Melandri, F., Scherer, D., Ballard, D., and Maniatis, T. (1995). Signal-induced site-specific phosphorylation targets I kappa B alpha to the ubiquitin-proteasome pathway, Genes Dev 9, 1586-97.
9. Crofford, L. J., Tan, B., McCarthy, C. J., and Hla, T. (1997). Involvement of nuclear factor kappa B in the regulation of cyclooxygenase-2 expression by interleukin-1 in rheumatoid synoviocytes, Arthritis Rheum 40, 226-36.
10. D'Haens, G., Van Deventer, S., Van Hogezand, R., Chalmers, D., Kothe, C., Baert, F., Braakman, T., Schaible, T., Geboes, K., and Rutgeerts, P. (1999). Endoscopic and histological healing with infliximab anti-tumor necrosis factor antibodies in Crohn's disease: A European multicenter trial, Gastroenterology 116, 1029-34.
11. Darmoul, D., Marie, J. C., Devaud, H., Gratio, V., and Laburthe, M. (2001). Initiation of human colon cancer cell proliferation by trypsin acting at protease-activated receptor-2, Br J Cancer 85, 772-9.
12. DiDonato, J., Mercurio, F., Rosette, C., Wu-Li, J., Suyang, H., Ghosh, S., and Karin, M. (1996). Mapping of the inducible IkappaB phosphorylation sites that signal its ubiquitination and degradation, Mol Cell Biol 16, 1295-304.
13. DuBois, R. N., Giardiello, F. M., and Smalley, W. E. (1996). Nonsteroidal anti-inflammatory drugs, eicosanoids, and colorectal cancer prevention, Gastroenterol Clin North Am 25, 773-91.
14. Eberhart, C. E., Coffey, R. J., Radhika, A., Giardiello, F. M., Ferrenbach, S., and DuBois, R. N. (1994). Up-regulation of cyclooxygenase 2 gene expression in human colorectal adenomas and adenocarcinomas, Gastroenterology 107, 1183-8.
15. Elder, D. J., Halton, D. E., Hague, A., and Paraskeva, C. (1997). Induction of apoptotic cell death in human colorectal carcinoma cell lines by a cyclooxygenase-2 (COX-2)-selective nonsteroidal anti-inflammatory drug: independence from COX-2 protein expression, Clin Cancer Res 3, 1679-83.
16. Elnemr, A., Ohta, T., Yachie, A., Kayahara, M., Kitagawa, H., Fujimura, T., Ninomiya, I., Fushida, S., Nishimura, G. I., Shimizu, K., and Miwa, K. (2001). Human pancreatic cancer cells disable function of Fas receptors at several levels in Fas signal transduction pathway, Int J Oncol 18, 311-6.

17. Engers, R., and Gabbert, H. E. (2000). Mechanisms of tumor metastasis: cell biological aspects and clinical implications, J Cancer Res Clin Oncol 126, 682-92.
18. Frisch, S. M., and Francis, H. (1994). Disruption of epithelial cell-matrix interactions induces apoptosis, J Cell Biol 124, 619-26.
19. Giri, D. K., and Aggarwal, B. B. (1998). Constitutive activation of NF-κB causes resistance to apoptosis in human cutaneous T cell lymphoma HuT-78 cells. Autocrine role of tumor necrosis factor and reactive oxygen intermediates, J Biol Chem 273, 14008-14.
20. Golab, J., Kozar, K., Kaminski, R., Czajka, A., Marczak, M., Switaj, T., Giermasz, A., Stoklosa, T., Lasek, W., Zagozdzon, R., et al. (2000). Interleukin 12 and indomethacin exert a synergistic, angiogenesis-dependent antitumor activity in mice, Life Sci 66, 1223-30.
21. Groden, J., Joslyn, G. Samowitz, W., Jones, D., Bhattacharyya, N., Spirio, L., Thliveris, A., Robertson, M., Egan, S., Meuth, M., and et al. (1995). Response of colon cancer cell lines to the introduction of APC, a colon-specific tumor suppressor gene, Cancer Res 55, 1531-9.
22. Han, S. Y., Choung, S. Y., Paik, I. S., Kang, H. J., Choi, Y. H., Kim, S. J., and Lee, M. O. (2000). Activation of NF-κB determines the sensitivity of human colon cancer cells to TNFalpha-induced apoptosis, Biol Pharm Bull 23, 420-6.
23. Hansen, E., Knuechel, R., Altmeppen, J., and Taeger, K. (1999). Blood irradiation for intraoperative autotransfusion in cancer surgery: demonstration of efficient elimination of contaminating tumor cells, Transfusion 39, 608-15.
24. Hansen, E., Wolff, N., Knuechel, R., Ruschoff, J., Hofstaedter, F., and Taeger, K. (1995). Tumor cells in blood shed from the surgical field, Arch Surg 130, 387-93.
25. He, T. C., Chan, T. A., Vogelstein, B., and Kinzler, K. W. (1999). PPARdelta is an APC-regulated target of nonsteroidal anti-inflammatory drugs, Cell 99, 335-45.
26. Henkel, T., Machleidt, T., Alkalay, I., Kronke, M., Ben-Neriah, Y., and Baeuerle, P. A. (1993). Rapid proteolysis of I kappa B-alpha is necessary for activation of transcription factor NF-κB, Nature 365, 182-5.
27. Higgins, K. A., Perez, J. R., Coleman, T. A., Dorshkind, K., McComas, W. A., Sarmiento, U. M., Rosen, C. A., and Narayanan, R. (1993). Antisense inhibition of the p65 subunit of NF-κB blocks tumorigenicity and causes tumor regression, Proc Natl Acad Sci USA 90, 9901-5.
28. Hsi, L. C., Baek, S. J., and Eling, T. E. (2000). Lack of cyclooxygenase-2 activity in HT-29 human colorectal carcinoma cells, Exp Cell Res 256, 563-70.
29. Huang, S., Pettaway, C. A., Uehara, H., Bucana, C. t)., and Fidler, I. J. (2001). Blockade of NF-κB activity in human prostate cancer cells is associated with suppression of angiogenesis, invasion, and metastasis, Oncogene 20, 4188-97.
30. Ichijo, H., Nishida, E., Irie, K., ten Dijke, P., Saitoh, M., Moriguchi, T., Takagi, M., Matsumoto, K., Miyazono, K., and Gotoh, Y. (1997). Induction of apoplosis by ASK1, a mammalian MAPKKK that activates SAPK/JNK and p38 signaling pathways, Science 275, 90-4.
31. Ilyas, M., Tomlinson, I. P., Rowan, A., Pignatelli, M., and Bodmer, W. F. (1997). Beta-catenin mutations in cell lines established from human colorectal cancers, Proc Natl Acad Sci USA 94, 10330-4.
32. Irmler, M., Thome, M., Hahne, M., Schneider, P., Hofmann, K., Steiner, V., Bodmer, J. L., Schroter, M., Burns, K., Mattmann, C., et al. (1997). Inhibition of death receptor signals by cellular FLIP, Nature 388, 190-5.
33. Jung, H. C., Eckmann, L., Yang, S. K., Panja, A., Fierer, J., Morzycka-Wroblewska, E., and Kagnoff, M. F. (1995). A distinct array of proinflammatory cytokines is expressed in human colon epithelial cells in response to bacterial invasion, J Clin Invest 95, 55-65.
34. Kreuz, S., Siegmund, D., Scheurich, P., and Wajant, H. (2001). NF-κB inducers upregulate cFLIP, a cycloheximide-sensitive inhibitor of death receptor signaling, Mol Cell Biol 21, 3964-73.
35. Kutchera, W., Jones, D. A., Matsunami, N., Groden, J., McIntyre, T. M., Zimmerman, G. A., White, R. L., and Prescott, S. M. (1996). Prostaglandin H synthase 2 is expressed abnormally in human colon cancer: evidence for a transcriptional effect, Proc Natl Acad Sci USA 93, 4816-20.
36. Lee, J. W., and Juliano, R. L. (2000). alpha5beta1 integrin protects intestinal epithelial cells from apoptosis through a phosphatidylinositol 3-kinase and protein kinase B-dependent pathway, Mol Biol Cell 11, 1973-87.
37. Liefers, G. J., Cleton-Jansen, A. M., van de Velde, C. J., Hennans, J., van Krieken, J. H., Cornelisse, C. J., and Tollenaar, R. A. (1998). Micrometastases and survival in stage II colorectal cancer, N Engl J Med 339, 223-8.
38. Liotta, L. A., Kleinerman, J., and Saidel, G. M. (1974). Quantitative relationships of intravascular tumor cells, tumor vessels, and pulmonary metastases following tumor implantation, Cancer Res 34, 997-1004.
39. Martin, G. S. (1996). Normal Cells and Cancer Cells. In Molecular Oncology, J. M. Bishop, and R. A. Weinberg, eds. (New York, Scientific American), pp. 13-40.
40. Mehes, G., Witt, A., Kubista, E., and Ambros, P. F. (2001). Circulating breast cancer cells are frequently apoptotic, Am J Pathol 159, 17-20.
41. Meredith, J. E., Jr., Fazeli, B., and Schwartz, M. A. (1 993). The extracellular matrix as a cell survival factor., Mol Biol Cell 4, 953-61.
42. Munemitsu, S., Albert, I., Souza, B., Rubinfeld, B., and Polakis, P. (1995). Regulation of intracellular beta-catenin levels by the adenomatous polyposis coli (APC) tumor-suppressor protein, Proc Natl Acad Sci USA 92, 3046-50.
43. Newton, R., Kuitert, L. M., Bergmann, M., Adcock, I. M., and Barnes, P. J. (1997a). Evidence for involvement of NF-κB in the transcriptional control of COX-2 gene expression by IL-1beta, Biochem Biophys Res Commun 237, 28-32.
44. Newton, R., Stevens, D. A., Hart, L. A., Lindsay, M., Adcock, I. M., and Barnes, P. J. (1997b). Superinduction of COX-2 mRNA by cycloheximide and interleukin-1 beta involves increased transcription and correlates with increased NF-κB and JNK activation, FEBS Lett 418, 135-8.
45. Nicolson, G. L. (1991). Gene expression, cellular diversification and tumor progression to the metastatic phenotype, Bioessays 13, 337-42.
46. Palombella, V. J., Rando, O. J., Goldberg, A. L., and Maniatis, T. (1994). The ubiquitin-proteasome pathway is required for processing the NF-κB 1 precursor protein and the activation of NF-κB, Cell 78, 773-85.
47. Peleg, II, Lubin, M. F., Cotsonis, G. A., Clark, W. S., and Wilcox, C. M. (1996). Long-term use of nonsteroidal anti-inflammatory drugs and other chemopreventors and risk of subsequent colorectal neoplasia, Dig Dis Sci 41, 1319-26.
48. Pierce, J. W., Schoenleber, R., Jesmok, G., Best, J., Moore, S. A., Collins, T., and Gerritsen, M. E. (1997). Novel inhibitors of cytokine-induced IkappaBalpha phosphorylation and endothelial cell adhesion molecule expression show anti-inflammatory effects in vivo, J Biol Chem 272, 21096-103.

49. Remacle-Bonnet, M. M., Garrouste, F. L., Heller, S., Andre, F., Marvaldi, J. L., and Pommier, G. J. (2000). Insulin-like growth factor-I protects colon cancer cells from death factor-induced apoptosis by potentiating tumor necrosis factor alpha-induced mitogen-activated protein kinase and nuclear factor kappaB signaling pathways, Cancer Res 60, 2007-17.

50. Renard, P., Ernest, I., Houbion, A., Art, M., Le Calvez, H., Raes, M., and Remacle, J. (2001). Development of a sensitive multi-well colorimetric assay for active NF-κB, Nucleic Acids Res 29; E21.

51. Rosette, C., and Karin, M. (1996). Ultraviolet light and osmotic stress: activation of the JNK cascade through multiple growth factor and cytokine receptors, Science 274, 1194-7.

52. Rubinfeld, B., Souza, B., Albert, I., Munemitsu, S., and Polakis, P. (1995). The APC protein and E-cadherin form similar but independent complexes with alpha-catenin beta-catenin, and plakoglobin, J Biol Chem 270, 5549-55.

53. Ryu, B. K., Lee, M. G., Chi, S. G., Kim, Y. W., and Park, J. H. (2001). Increased expression of cFLIP(L) in colonic adenocarcinoma, J Pathol 194, 15-9.

54. Schmedtje, J. F., Jr., Ji, Y. S., Liu, W. L., DuBois, R. N., and Runge, M. S. (1997). Hypoxia induces cyclooxygenase-2 via the NF-κB p65 transcription factor in human vascular endothelial cells, J Biol Chem 272, 601-8.

55. Schwartz, S. A., Hernandez, A., and Evers, B. M. (1999). The role of NF-κB/IκB proteins in cancer: implications for novel treatment strategies., Surgical Oncology 8, 143-153.

56. Shanmugathasan, M., and Jothy, S. (2000). Apoptosis, anoikis and their relevance to the pathobiology of colon cancer, Pathol Int 50, 273-9.

57. Shao, J., Sheng, H., Inoue, H., Morrow, J. D., and DuBois, R. N. (2000). Regulation of constitutive cyclooxygenase-2 expression in colon carcinoma cells, J Biol Chem 275, 33951-6.

58. Sheng, H., Shao, J., Kirkland, S. C., Isakson, P., Coffey, R. J., Morrow, J., Beauchamp, R. D., and DuBois, R. N. (1997). Inhibition of human colon cancer cell growth by selective inhibition of cyclooxygenase-2, J Clin Invest 99, 2254-9.

59. Shiff, S. J., Qiao, L., Tsai, L. L., and Rigas, B. (1995). Sulindac sulfide, an aspirin-like compound, inhibits proliferation, causes cell cycle quiescence, and induces apoptosis in HT-29 colon adenocarcinoma cells, J Clin Invest 96, 491-503.

60. Shinohara, H., Killion, J. J., Kuniyasu, H., Kumar, R., and Fidler, I. J. (1998). Prevention of intestinal toxic effects and intensification of irinotecan's therapeutic efficacy against murine colon cancer liver metastases by oral administration of the lipopeptide JBT 3002, Clin Cancer Res 4, 2053-3.

61. Shureiqi, I., Chen, D., Lee, J. J., Yang, P., Newman, R. A., Brenner, D. E., Lotan, R., Fischer, S. M., and Lippman, S. M. (2000). 15-LOX-1: a novel molecular target of nonsteroidal anti-inflammatory drug-induced apoptosis in colorectal cancer cells, J Natl Cancer Inst 92, 1136-42.

62. Shureiqi, I., Wojno, K. J., Poore, J. A., Reddy, R. G., Moussalli, M. J., Spindle, S. A., Greenson, J. K., Normolle, D., Hasan, A. A., Lawrence, T. S., and Brenner, D. E. (1999). Decreased 13-S-hydroxyoctadecadienoic acid levels and 15-lipoxygenase-1 expression in human colon cancers, Carcinogenesis 20, 1985-95.

63. Singh, A. K., and Trotman, B. W. (1998). Use and safety of aspirin in the chemoprevention of colorectal cancer, J Assoc Acad Minor Phys 9, 40-4.

64. Sinicrope, F. A., Pazdur, R., and Levin, B. (1996). Phase I trial of sulindac plus 5-fluorouracil and levamisole: potential adjuvant therapy for colon carcinoma, Clin Cancer Res 2, 37-41.

65. Smalley, W. E., and DuBois, R. N. (1997). Colorectal cancer and nonsteroidal anti-inflammatory drugs, Adv Pharmacol 39, 1-20.

66. Sokoloski, J. A., Sartorelli, A. C., Rosen, C. A., and Narayanan, R. (1993). Antisense oligonucleotides to the p65 subunit of NF-κB block CD11b expression and alter adhesion properties of differentiated HL-60 granulocytes, Blood 82, 625-32.

67. Stehlik, C., de Martin, R., Kumabashiri, I., Schmid, J. A., Binder, B. R., and Lipp, J. (1998). Nuclear factor (NF)-kappaB-regulated X-chromosome-linked iap gene expression protects endothelial cells from tumor necrosis factor alpha-induced apoptosis, J Exp Med 188, 211-6.

68. Strater, J., Wedding, U., Barth, T. F., Koretz, K., Elsing, C., and Moller, P. (1996). Rapid onset of apoptosis in vitro follows disruption of beta 1-integrin/matrix interactions in human colonic crypt cells, Gastroenterology 110, 1776-84.

69. Tepper, C. G., and Seldin, M. F. (1999). Modulation of caspase-8 and FLICE-inhibitory protein expression as a potential mechanism of Epstein-Barr virus tumorigenesis in Burkitt's lymphoma, Blood 94, 1727-37.

70. Traenckner, E. B., Pahl, H. L., Henkel, T., Schmidt, K. N., Wilk, S., and Baeuerle, P. A. (1995). Phosphorylation of human I kappa B-alpha on serines 32 and 36 controls I kappa B-alpha proteolysis and NF-κB activation in response to diverse stimuli, Embo J 14, 2876-83.

71. Tsuji, S., Kawano, S., Sawaoka, H., Takei, Y., Kobayashi, I., Nagano, K., Fusamoto, H., and Kamada, T. (1996). Evidences for involvement of cyclooxygenase-2 in proliferation of two gastrointestinal cancer cell lines, Prostaglandins Leukot Essent Fatty Acids 55, 179-83.

72. Tsujii, M., and DuBois, R. N. (1995). Alterations in cellular adhesion and apoptosis in epithelial cells overexpressing prostaglandin endoperoxide synthase 2, Cell 83, 493-501.

73. Wang, C. Y., Cusack, J. C., Jr., Liu, R., and Baldwin, A. S., Jr. (1999). Control of inducible chemoresistance: enhanced anti-tumor therapy through increased apoptosis by inhibition of NF-κB, Nat Med 5, 412-7.

74. Wang, C. Y., Mayo, M. W., Korneluk, R. G., Goeddel, D. V., and Baldwin, A. S., Jr. (1998). NF-κB antiapoptosis: induction of TRAF1 and TRAF2 and c-IAP1 and c-IAP2 to suppress caspase-8 activation, Science 281, 1680-3.

75. Weiss, L. (1985). Metastatic inefficiency. In Liver Metastasis, L. Weiss, and H. Gilbert, eds. (Boston, Hall), pp. 126-157.

76. Wu, M. X., Ao, Z., Prasad, K. V., Wu, R., and Schlossman, S. F. (1998). IEX-IL, an apoptosis inhibitor involved in NF-κB-mediated cell survival, Science 281, 998-1001.

77. Yamamoto, Y., Yin, M. J., Lin, K. M., and Gaynor, R. B. (1999). Sulindac inhibits activation of the NF-κB pathway, J Biol Chem 274, 27307-14.

78. Yin, M. J., Yamamoto, Y., and Gaynor, R. B. (1998). The anti-inflammatory agents aspirin and salicylate inhibit the activity of I(kappa)B kinase-beta, Nature 396, 77-80.

Throughout this application, various publications are referenced. The disclosures of these publications in their entireties are hereby incorporated by reference into this application in order to more fully describe the state of the art. The references disclosed are also individually and specifically incorporated by reference herein for the material contained in them that is discussed in the sentence in which the reference is relied upon.

What is claimed is:

1. A method for inhibiting reseeding of HT-29 colon cancer cells during or after surgical resection of a tumor: comprising administering to a subject within 10 days of the resection, a compound having the structure

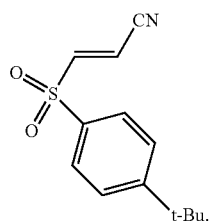

2. The method of claim 1, wherein the compound is administered prior to the resection.

3. The method of claim 1, wherein the compound is administered after the resection.

4. The method of claim 1, wherein the compound is administered within 5 days of the resection.

5. The method of claim 1, wherein the compound is administered within 1 day of the resection.

6. The method of claim 1, wherein the compound is administered within 10 hours of the resection.

7. The method of claim 1, wherein the compound is administered within 1 hour of the resection.

8. The method of claim 1, wherein the compound is administered within 0.5 hours of the resection.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
agttgagggg actttcccag gc                                              22

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
gggactttcc                                                            10
```